United States Patent
Ogihara et al.

(10) Patent No.: US 9,069,247 B2
(45) Date of Patent: *Jun. 30, 2015

(54) SILICON-CONTAINING SURFACE MODIFIER, RESIST LOWER LAYER FILM-FORMING COMPOSITION CONTAINING THE SAME, AND PATTERNING PROCESS

(71) Applicant: SHIN-ETSU CHEMICAL CO., LTD., Tokyo (JP)

(72) Inventors: Tsutomu Ogihara, Jyoetsu (JP); Takafumi Ueda, Jyoetsu (JP); Yoshinori Taneda, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/747,125

(22) Filed: Jan. 22, 2013

(65) Prior Publication Data

US 2013/0210229 A1    Aug. 15, 2013

(30) Foreign Application Priority Data

Feb. 14, 2012    (JP) .................................. 2012-029230

(51) Int. Cl.
| | | |
|---|---|---|
| G03F 7/075 | (2006.01) | |
| G03F 7/11 | (2006.01) | |
| G03F 7/36 | (2006.01) | |
| G03F 7/40 | (2006.01) | |
| H01L 21/306 | (2006.01) | |
| C07F 7/18 | (2006.01) | |
| C09D 183/06 | (2006.01) | |
| C08L 83/06 | (2006.01) | |
| C08G 77/14 | (2006.01) | |
| G03F 7/20 | (2006.01) | |

(52) U.S. Cl.
CPC ............ *G03F 7/0752* (2013.01); *H01L 21/306* (2013.01); *C07F 7/1804* (2013.01); *G03F 7/36* (2013.01); *C07F 7/1836* (2013.01); *C07F 7/184* (2013.01); *C09D 183/06* (2013.01); *C08L 83/06* (2013.01); *G03F 7/0757* (2013.01); *G03F 7/11* (2013.01); *C08G 77/14* (2013.01); *G03F 7/0751* (2013.01); *G03F 7/2041* (2013.01); *G03F 7/40* (2013.01)

(58) Field of Classification Search
None
See application file for complete search history.

(56) References Cited

U.S. PATENT DOCUMENTS

| | | |
|---|---|---|
| 4,510,136 A | 4/1985 | Moberg |
| 4,902,603 A | 2/1990 | Slater et al. |
| 5,178,989 A | 1/1993 | Heller et al. |
| 5,508,358 A | 4/1996 | Ono et al. |
| 5,632,910 A | 5/1997 | Nagayama et al. |
| 7,651,829 B2 | 1/2010 | Hamada et al. |
| 2001/0016635 A1 | 8/2001 | Evain et al. |
| 2002/0187422 A1 | 12/2002 | Angelopoulos et al. |
| 2003/0191268 A1 | 10/2003 | Iwasawa et al. |
| 2003/0235786 A1 | 12/2003 | Krishnamurthy et al. |
| 2004/0058275 A1 | 3/2004 | Neef et al. |
| 2004/0241579 A1 | 12/2004 | Hamada et al. |
| 2005/0048395 A1 | 3/2005 | Kobayashi et al. |
| 2005/0112383 A1 | 5/2005 | Tanaka et al. |
| 2006/0019195 A1 | 1/2006 | Hatakeyama et al. |
| 2006/0024980 A1 | 2/2006 | Tsuchiya et al. |
| 2006/0040206 A1 | 2/2006 | Nakashima et al. |
| 2007/0134916 A1 | 6/2007 | Iwabuchi et al. |
| 2007/0178318 A1 | 8/2007 | Tanaka et al. |
| 2007/0203275 A1 | 8/2007 | Kikuchi et al. |
| 2007/0231738 A1 | 10/2007 | Kaneko et al. |
| 2007/0238300 A1 | 10/2007 | Ogihara et al. |
| 2008/0026322 A1 | 1/2008 | Ogihara et al. |
| 2009/0011366 A1 | 1/2009 | Tsubaki et al. |

(Continued)

FOREIGN PATENT DOCUMENTS

| | | |
|---|---|---|
| EP | 1 628 160 A2 | 2/2006 |
| EP | 1 798 599 A1 | 6/2007 |

(Continued)

OTHER PUBLICATIONS

Machine-assisted English translation for JP 5590354 B2, which is equivalent to Kanno et al (WO 2011/105368 A1) (2011).*

(Continued)

*Primary Examiner* — Sin Lee
(74) *Attorney, Agent, or Firm* — Oliff PLC

(57) ABSTRACT

The present invention provides a silicon-containing surface modifier containing one or more repeating units each represented by the following general formula (A), or one or more partial structures each represented by the following general formula (C):

It is aimed at providing a resist lower layer film which is usable for a resist pattern formed of a hydrophilic organic compound to be obtained in a negative development.

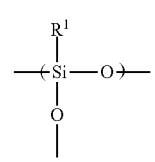

(A)

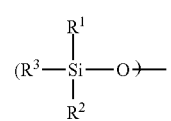

(C)

12 Claims, 1 Drawing Sheet

(56) References Cited

U.S. PATENT DOCUMENTS

| | | | |
|---|---|---|---|
| 2009/0136869 A1 | 5/2009 | Ogihara et al. | |
| 2010/0040972 A1 | 2/2010 | Tarutani et al. | |
| 2010/0041805 A1 | 2/2010 | Amidaiji et al. | |
| 2010/0086872 A1 | 4/2010 | Ogihara et al. | |
| 2012/0276483 A1* | 11/2012 | Ogihara et al. | 430/319 |
| 2013/0005150 A1 | 1/2013 | Ogihara et al. | |
| 2013/0045601 A1 | 2/2013 | Ogihara et al. | |
| 2013/0101942 A1 | 4/2013 | Tanaka et al. | |

FOREIGN PATENT DOCUMENTS

| | | |
|---|---|---|
| EP | 1 845 132 A2 | 10/2007 |
| EP | 2 103 655 A1 | 9/2009 |
| EP | 2 138 898 A1 | 12/2009 |
| EP | 2 172 808 A1 | 4/2010 |
| EP | 2 500 775 A2 | 9/2012 |
| EP | 2 518 562 A2 * | 10/2012 |
| EP | 2 540 780 A1 | 1/2013 |
| JP | A-07-181688 | 7/1995 |
| JP | A-07-183194 | 7/1995 |
| JP | A-11-258813 | 9/1999 |
| JP | A-2000-053921 | 2/2000 |
| JP | A-2004-153125 | 5/2004 |
| JP | A-2005-128509 | 5/2005 |
| JP | A-2005-173552 | 6/2005 |
| JP | A-2005-520354 | 7/2005 |
| JP | A-2005-537502 | 12/2005 |
| JP | A-2006-508377 | 3/2006 |
| JP | A-2006-251369 | 9/2006 |
| JP | A-2006-317864 | 11/2006 |
| JP | A-2007-199653 | 8/2007 |
| JP | A-2007-226170 | 9/2007 |
| JP | A-2007-297590 | 11/2007 |
| JP | A-2007-302873 | 11/2007 |
| JP | A-2008-281974 | 11/2008 |
| JP | A-2008-281980 | 11/2008 |
| JP | 2009-025707 A | 2/2009 |
| JP | A-2009-053657 | 3/2009 |
| JP | A-2009-126940 | 6/2009 |
| JP | A-2010-085893 | 4/2010 |
| JP | B2-4716037 | 7/2011 |
| JP | 2013-083964 A | 5/2013 |
| TW | 2008-06746 | 2/2008 |
| WO | WO 2004/007192 A1 | 1/2004 |
| WO | WO 2011/105368 A1 | 9/2011 |

OTHER PUBLICATIONS

Jun. 19, 2013 extended European Search Report issued in European Patent Application No. EP 13 00 0600.0.
May 20, 2014 Office Action issued in Japanese Patent Application No. 2012-029230 (with partial translation).
Jan. 6, 2015 Office Action issued in Japanese Patent Application No. 2012-029228.
Oct. 9, 2012 Extended European Search Report issued in European Patent Application No. 12004626.3.
Jul. 23, 2014 Office Action issued in European Patent Application No. 12 004 626.3.
Aug. 19, 2014 Notification of Reasons for Refusal issued in Japanese Patent Application No. 2011-220708 (with partial translation).
Database CA [Online], Ogihara et al., "A Patterning Process," Oct. 31, 2012, XP002698566.
Database Reaxys [Online], Sumitomo Chemical Company, Limited, "Organic Silicon-Based Compound and Method of Producing the Same," Aug. 30, 2007, XP002698567.
Temtsin et al., "Aromatic PMOs: tolyl, xylyl and dimethoxyphenyl groups integrated within the channel walls of hexagonal mesoporous silicas," *Journal of Materials Chemistry*, vol. 11, No. 12, Oct. 23, 2001, pp. 3202-3206.
Database Reaxys [Online], Manoso et al., "Improved Synthesis of Aryltrialkoxysilanes via Treatment of Aryl Grignard or Lithium Reagents with Tetraalkyl Orthosilicates," 2004, XP002698568.
Database Reaxys [Online], Seganish et al., "Efforts Directed toward the Synthesis of Colchicine: Application of Palladium-Catalyzed Siloxane Cross-Coupling Methodology," 2005, XP002698569.
Database CA [Online], Moberg, William K., "Fungicidal 1-(silylmethyl)-1,2,4-triazole derivatives," 1986, XP002698570.
Database CA [Online], Virtanen et al., "Organosilane and their hydrolytic polymers as surface treatment agents for use in chromatography and electronics," 1987, XP002698571.
Database CA [Online], Harkonen et al., "External silane donors in Ziegler-Natta catalysis. An approach to the optimum structure of the donor," 1991, XP002698572.
Database CA [Online], O'Dell, R., "A convenient synthesis of arylbis (ethyltrifluorosiliconate)s," 1995, XP002698573.
Database CA [Online], Evain et al., "Alpha-olefin polymerization catalyst system containing an aromatic silane compound," 2001, XP002698574.
Jun. 24, 2013 Extended European Search Report issued in European Application No. 13002020.9.
Oct. 9, 2014 Office Action issued in European Patent Application No. 13002020.9.
Patai, S. et al., "The Chemistry of Organic Silicon Compounds," 1989, John Wiley & Sons, pp. 909-916.
Aug. 12, 2013 Extended European Search Report issued in European Application No. 12002878.2.
Jan. 20, 2014 Taiwanese Office Action issued in Taiwanese Patent Application No. 101115187 (with partial English-language translation).
U.S. Appl. No. 14/107,841 in the name of Ogihara et al., filed Dec. 16, 2013.
Maenhoudt et al., "Double Patterning scheme for sub-0.25 k1 single damascene structures at NA=0.75, $\lambda$=193nm", *Proceedings of SPIE*, 2005, vol. 5754, pp. 1508-1518.
Nakamura et al., "Contact Hole Formation by Multiple Exposure Technique in Ultra-low k1 Lithography", *Proceedings of SPIE*, 2004, vol. 5377, pp. 255-263.
Jun. 13, 2013 Extended European Search Report issued in European Patent Application No. EP 13000599.4.
Mar. 17, 2014 Office Action issued in U.S. Appl. No. 13/524,669.
Jul. 9, 2014 Office Action issued in U.S. Appl. No. 13/524,669.
Oct. 21, 2014 Office Action issued in U.S. Appl. No. 13/854,622.
Feb. 10, 2014 Office Action issued in U.S. Appl. No. 13/430,319.
Jul. 17, 2013 Office Action issued in U.S. Appl. No. 13/430,319.
Aug. 29, 2014 Office Action issued in U.S. Appl. No. 13/747,154.
U.S. Appl. No. 13/747,154 in the name of Ogihara et al., filed Jan. 22, 2013.
U.S. Appl. No. 14/107,500 in the name of Ogihara et al., filed Dec. 16, 2013.
U.S. Appl. No. 13/854,622 in the name of Ogihara et al., filed Apr. 1, 2013.
U.S. Appl. No. 13/430,319 in the name of Ogihara et al., filed Mar. 26, 2012.
Dec. 24, 2014 Office Action issued in Japanese Application No. 2012-029230.
Feb. 25, 2015 Office Action issued in U.S. Appl. No. 14/107,500.
Mar. 27, 2015 Office Action issued in European Application No. 13000599.4.

* cited by examiner

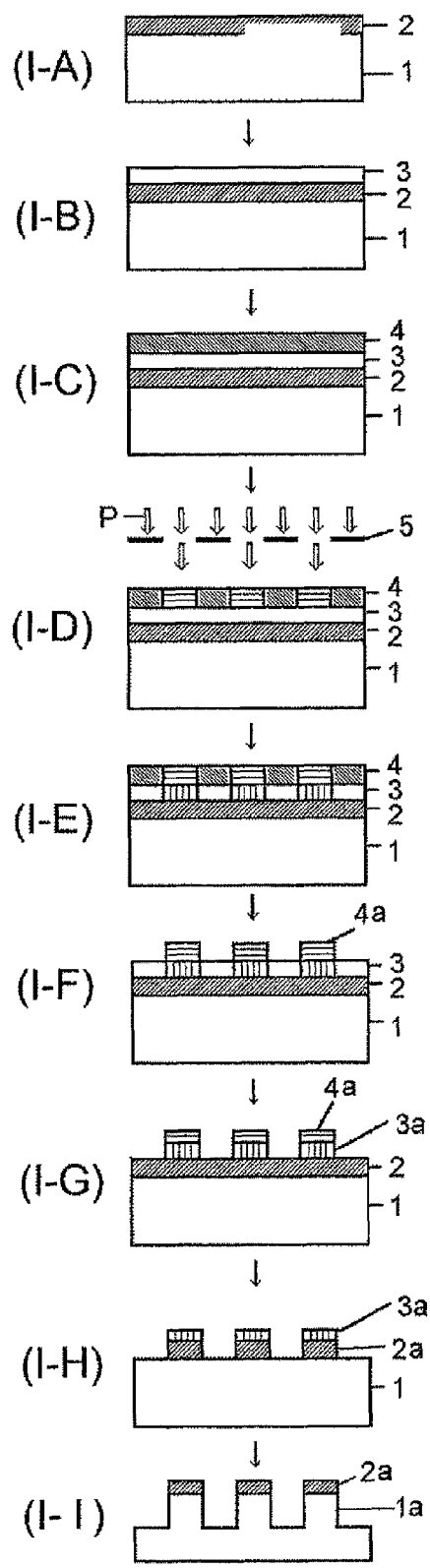

SILICON-CONTAINING SURFACE MODIFIER, RESIST LOWER LAYER FILM-FORMING COMPOSITION CONTAINING THE SAME, AND PATTERNING PROCESS

BACKGROUND OF THE INVENTION

1. Field of the Invention

The present invention relates to a silicon-containing surface modifier, a resist lower layer film-forming composition containing the same, and a patterning process.

2. Description of the Related Art

Widely adopted as exposure light to be used upon resist pattern formation in 1980's, were a g-line (436 nanometers) or an i-line (365 nanometers) of a mercury lamp. As means for further scaling-down, shifting to a shorter wavelength of exposure, light was assumed to be effective, so that in a mass-production process after a DRAM (Dynamic Random Access Memory) of a 64M bit (processing dimension of less than 0.25 μm) in 1990's, a KrF excimer laser (248 nm) at a shorter wavelength was used as an exposure light source instead of the i-line. However, in production of DRAMs at integration degrees of 256M, 1G, and higher which require a finer processing technique (processing dimension of 0.2 μm or less), light sources at shorter wavelength were required, thereby resulting in earnest investigations of photolithography adopting an ArF excimer laser (193 nm) in the past ten years. Although the ArF lithography was initially intended to be firstly applied to a device fabrication of a 180 nm node device, the KrF excimer lithography was prolonged in life to a mass-production of a 130 nm node device, such that the ArF lithography was firstly and fully applied to a 90 nm node. Further, such a technique was combined with a lens having an NA increased to as great as 0.9, thereby conducting mass-production of a 65 nm node device. Further shortening of wavelength of the exposure light is progressing in the next 45-nm node device; and for that, the $F_2$ lithography with 157 nm wavelength became a candidate. Unfortunately, the development of $F_2$ lithography was abandoned, due to various burdens such as: an increased cost of a scanner because of usage of a large amount of expensive $CaF_2$ single crystal for a projection lens; a modification of an optical system accompanying to introduction of a hard pellicle instead of a soft pellicle exhibiting an extremely low durability; a deteriorated resistance of a resist film, against etching; and the like; resulting in alternative introduction of ArF liquid immersion lithography.

In the ArF immersion lithography, such a water having a refractive index of 1.44 was introduced between a projection lens and a wafer by a partial filling manner, thereby enabling a high-speed scanning to conduct mass-production of a 45 nm node device by means of a lens having an NA of about 1.3.

Meanwhile, as a candidate of lithography technique for a 32 nm node, vacuum ultraviolet light (EUV) at a wavelength of 13.5 nm has been mentioned. However, the EUV lithography is accompanied by a pile of problems to be overcome, such as a laser to be increased in output, a resist film to be increased in sensitivity, a resolution to be enhanced, a line edge roughness (LER) to be lowered, an MoSi lamination mask to be free of defects, reflective mirror aberrations to be lowered, and the like.

In turn, the high refractive index immersion lithography as another candidate as a technique for a 32 nm node has been abandoned in development, because the LUAG as a candidate of a high refractive index lens exhibits a lower transmittance, and it has been impossible to obtain a liquid having a refractive index increased to a targeted value of 1.8.

As described above, the light exposure having been used as a general-purpose technique is now approaching a limit of an essential resolution inherent to the wavelength of a light source. As such, attention has been again directed to an organic solvent development configured to form such an extremely fine hole pattern by virtue of a negative tone obtained by an organic solvent development, which hole pattern has not been attained insofar as based on a conventional patterning process by a positive tone to be obtained by alkaline development. The organic solvent development is a process configured to adopt a positive resist composition having a higher resolution, and to conduct the organic solvent development, thereby obtaining a negative pattern. Further, even such an investigation is being progressed, to combine two times of developments, i.e., the alkaline development and the organic solvent development, so as to obtain a twice higher resolving power.

Usable as such an ArF resist composition for developing a negative tone by an organic solvent, is a conventional positive ArF resist composition, patterning processes for which are described in Patent Documents 1 to 3, for example.

One of techniques for transferring the thus formed negative tone pattern onto a substrate, is a multi-layer resist method. This technique is configured to: provide, an intermediate film such as a silicon-containing resist lower layer film, which is different in etching selectivity from a photoresist film, i.e., from a resist upper layer film, between the resist upper layer film and a substrate to be processed; obtain a pattern in the resist upper layer film; subsequently transfer the thus obtained pattern onto the resist lower layer film by dry etching, by using the upper layer resist pattern as a dry etching mask; and transfer the thus obtained pattern onto the substrate to be processed, by dry etching, by using the lower layer resist pattern as a dry etching mask.

Examples of the silicon-containing resist lower layer film to be used in such a multi-layer resist method include: a silicon-containing inorganic film based on CVD, such as a $SiO_2$ film (Patent Document 4, for example), and a SiON film (Patent Document 5, for example); a film to be obtained by spin coating, such as an SOG (spin-on-glass) film (Patent Document 6, for example), and a crosslinkable silsesquioxane film (Patent Document 7, for example); and the like.

Patent Document 1: JP2008-281974A
Patent Document 2: JP2008-281980A
Patent Document 3: JP2009-53657A
Patent Document 4: JP7-183194A
Patent Document 5: JP7-181688A
Patent Document 6: JP2007-302873A
Patent Document 7: JP2005-520354A

SUMMARY OF THE INVENTION

However, unlike the positive development (alkaline development) configured to form a resist pattern comprising a hydrophobic compound which is insoluble in an alkaline developer, the negative development (organic solvent development) is configured to form a resist pattern comprising a hydrophilic organic compound having an acidic carboxyl group and the like at a higher concentration, by means of a deprotection reaction. Thus, such a negative development leads to occurrence of pattern collapse insofar as using the conventional resist lower layer film, thereby failing to sufficiently exhibit the performance of the upper layer resist in case of the negative development.

The present invention has been attained in view of the above circumstances, and it is therefore an object of the present invention to provide a resist lower layer film which is usable for a resist pattern formed of a hydrophilic organic compound to be obtained in a negative development.

To solve the above problem, the present invention provides a silicon-containing surface modifier containing one or more repeating units each represented by the following general formula (A), or one or more partial structures each represented by the following general formula (C):

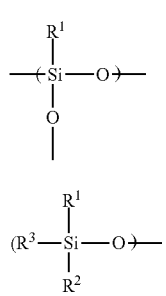

wherein
$R^1$ represents an organic group having a hydroxyl group or carboxylic acid group; and
$R^2$ and $R^3$ represent each independently the same as $R^1$, a hydrogen atom, or a monovalent organic group having 1 to 30 carbon atoms.

The surface modifier of the present invention provides such a contact angle of the resist lower layer film, which is closer to a contact angle of the negatively developed pattern of the upper layer resist at its exposed portion. This improves an adhesion of the resist lower layer film, even with the upper layer resist pattern obtained by the negative development process, thereby enabling to prevent a pattern collapse even in a thin line pattern.

Further, it is possible that the silicon-containing surface modifier further contains repeating units each represented by the following general formula (B),

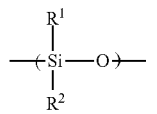

wherein $R^1$ and $R^2$ represent the same as the above.

Containment of the repeating units each represented by the general formula (B) enables to further widen the freedom degree of the design of the silicon-containing surface modifier, thereby adapting to pattern formations using various photoresists, respectively.

Furthermore, the present invention provides a silicon-containing resist lower layer film-forming composition containing the above-described silicon-containing surface modifier, and a polysiloxane compound.

In this way, the silicon-containing surface modifier of the present invention is added into the polysiloxane compound, thereby enabling to provide the silicon-containing resist lower layer film-forming composition for providing a silicon-containing resist lower layer film which is free of occurrence of pattern collapse even when combined with a negative development.

It is preferable that the polysiloxane compound contains a component derived from a tetrafunctional hydrolyzable monomer, in an amount of 70 mole % or more of the polysiloxane.

When the polysiloxane compound contains a component derived from a tetrafunctional hydrolyzable monomer, in an amount of 70 mole % or more of the polysiloxane, the silicon-containing surface modifier is apt to be concentratedly present at a surface of a resist lower layer film upon formation thereof, thereby enabling to form the silicon-containing resist lower layer film which allows for formation of a resist pattern having a lower roughness.

Further, it is possible that the composition of the present invention further contains a solvent having a boiling point of 180° C. or higher.

Containment of the solvent having a high boiling point of 180° C. or higher enables to form a resist lower layer film which is excellent in adhesion with the upper layer resist pattern.

Furthermore, the present invention provides a patterning process comprising the steps of:

using a coating type of organic lower layer film material, to form a lower organic layer film on a substance to be processed;

using the above-described silicon-containing resist lower layer film-forming composition, to form a silicon-containing resist lower layer film on the lower organic layer film;

using a chemically amplified resist composition, to form a photoresist film on the silicon-containing resist lower layer film;

heat-treating the photoresist film, then exposing the photoresist film to a high energy beam, and subsequently using an organic solvent-based developer to dissolve a non-exposed portion of the photoresist film, thereby forming a negative pattern through the photoresist film;

transferring the negative pattern formed through the photoresist film onto the silicon-containing resist lower layer film by dry etching, by using the photoresist film as a mask;

transferring the thus obtained resist lower layer film pattern onto the lower organic layer film by dry etching, by using the resist lower layer film as a mask; and transferring the thus obtained lower organic layer film pattern onto the substance to be processed, by dry etching, by using the lower organic layer film as a mask.

Moreover, the present invention provides a patterning process comprising the steps of:

forming an organic hard mask containing carbon as a main component, on a substance to be processed, by a CVD technique;

using the above-described silicon-containing resist lower layer film-forming composition, to form a silicon-containing resist lower layer film on the organic hard mask;

using a chemically amplified resist composition, to form a photoresist film on the silicon-containing resist lower layer film;

heat-treating the photoresist film, then exposing the photoresist film to a high energy beam, and subsequently using an organic solvent-based developer to dissolve a non-exposed portion of the photoresist film, thereby forming a negative pattern through the photoresist film;

transferring the negative pattern formed through the photoresist film onto the silicon-containing resist lower layer film by dry etching, by using the photoresist film as a mask;

transferring the thus obtained resist lower layer film pattern onto the organic hard mask by dry etching, by using the resist lower layer film as a mask; and transferring the thus obtained organic hard mask pattern onto the substance to be processed, by dry etching, by using the organic hard mask as a mask.

When the negative pattern is formed while using the resist lower layer film-forming composition of the present invention, it is possible to form the pattern formed of the photoresist on the substrate without causing a size conversion difference, by optimizing the combination with the CVD film or lower organic layer film as described above.

It is preferable in the negative patterning process to adopt, as the substance to be processed, a semiconductor device substrate itself, or a semiconductor device substrate formed thereon with any one of a metal film, an alloy film, a metal carbide film, a metal oxide film, a metal nitride film, a metal oxide carbide film, and a metal oxide nitride film.

Further, it is preferable in the patterning process that the substance to be processed includes a constituent metal which is any one of silicon, gallium, titanium, tungsten, hafnium, zirconium, chromium, germanium, copper, aluminum, and iron, or which is an alloy of one or more of these metals.

Using the patterning process of the present invention enables to process such a substance to be processed as noted above, thereby forming a pattern.

As explained above, by using the resist lower layer film formed by adopting the resist lower layer film-forming composition containing the silicon-containing surface modifier of the present invention, it is enabled to form such a resist pattern even by negative development (organic solvent development) which resist pattern is excellent in adherence with the resist lower layer film to thereby prevent occurrence of collapse of the pattern of the former, and which resist pattern is also excellent in surface roughness. Further, since the resist lower layer film is allowed to obtain a higher etching selectivity to the organic material, it is possible to successively transfer the formed photoresist pattern onto the silicon-containing resist lower layer film, and onto the lower organic layer film or CVD organic hard mask, by a dry etching process. In this respect, it is to be particularly noted that the recent semiconductor device production process progressed in scaling-down, tends to use a decreased thickness of photoresist film so as to prevent collapse of a photoresist pattern after development, thereby making it difficult to transfer the pattern to a resist lower layer film. Nonetheless, adopting the silicon-containing resist lower layer film-forming composition to form a resist lower layer film, allows to restrict a deformation of a photoresist pattern during dry etching to thereby transfer the pattern to a substrate with a higher precision, even when a thinner photoresist film is used as an etching mask.

BRIEF DESCRIPTION OF THE ACCOMPANYING DRAWINGS

FIG. 1 is a flow diagram of a patterning process according to the present invention.

DETAILED DESCRIPTION OF THE PREFERRED EMBODIMENTS

The present invention will be explained more specifically.

In case of a conventional positive photoresist, the film property of a photoresist film before exposure is the same as the film property of a photoresist pattern (hereinafter called "positive pattern") formed by alkaline development after exposure. As such, contact angles with pure water (hereinafter each simply called "contact angle") of the positive pattern and resist lower layer film are caused to approximate each other so as to improve an adhesion therebetween, thereby bringing about effects to improve an adhesion between the positive pattern and the resist lower layer film and to lower the roughness.

However, comparing a film property of a photoresist film before exposure with a film property of a negative pattern after exposure in case of a pattern (hereinafter called "negative pattern") to be obtained by negative development, acid-labile groups in the negative pattern have been removed by an acid generated by exposure in a manner to increase the number of hydrophilic groups such as a carboxyl group, a phenolic hydroxyl group, and the like, resulting in that the contact angle of the negative pattern has been changed to a hydrophilic side, i.e., to a lower value than a value of the contact angle of the photoresist film before exposure. As such, it has become apparent that, when the conventional resist lower layer film for a positive pattern is directly used, which film has a contact angle matched with a contact angle of a photoresist film before exposure, in case of the patterning process configured to use negative development, or in case of a patterning process configured to use both negative development and positive development, there is caused a discrepancy between the contact angle of the negative pattern after exposure and the contact angle of the resist lower layer film in a manner to cause collapse of the negative pattern, and influence on the roughness thereof.

Then, the present inventors have found out that such a resist lower layer film possibly made to have a contact angle approximated to a contact angle of a photoresist film after exposure, is allowed to possess an optimum surface state in both processes. Consequently, the present inventors have found out that it is possible to obtain a composition for forming a silicon-containing resist lower layer film having a contact angle analogous to a contact angle of a resist pattern, by blending a silicon-containing surface modifier containing an organic group having a hydroxyl group or carboxylic acid group into the resist lower layer film-forming composition at an appropriate ratio, thereby narrowly completing the present invention.

Namely, the silicon-containing surface modifier of the present invention is characterized in that the same contains one or more repeating units (hereinafter called "repeating units (A)" in some cases) each represented by the following general formula (A), or one or more partial structures (hereinafter called "partial structures (C)" in some cases) each represented by the following general formula (C),

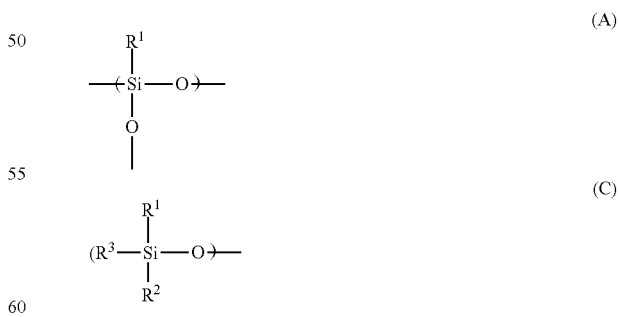

wherein $R^1$ represents an organic group having a hydroxyl group or carboxylic acid group; and $R^2$ and $R^3$ represent each independently the same as $R^1$, a hydrogen atom, or a monovalent organic group having 1 to 30 carbon atoms.

Here, the term "organic group" used in the present invention implies a group containing a carbon atom, which group may further include a hydrogen atom, in addition, a nitrogen, oxygen, sulfur, silicon, or halogen atom.

Further, it is possible that the silicon-containing surface modifier of the present invention further contains repeating units (hereinafter called "repeating units (B)" in some cases) each represented by the following general formula (B),

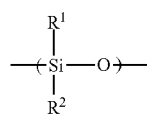

wherein $R^1$ and $R^2$ represent the same as the above.

Examples of the organic group represented as $R^1$ having a hydroxyl group or carboxylic acid group in the repeating units (A), (B) and partial structures (C) constituting the silicon-containing surface modifier of the present invention, include those structures represented by the following formulae, respectively. The following formulae each include a mark (Si) so as to show a bonding site to Si.

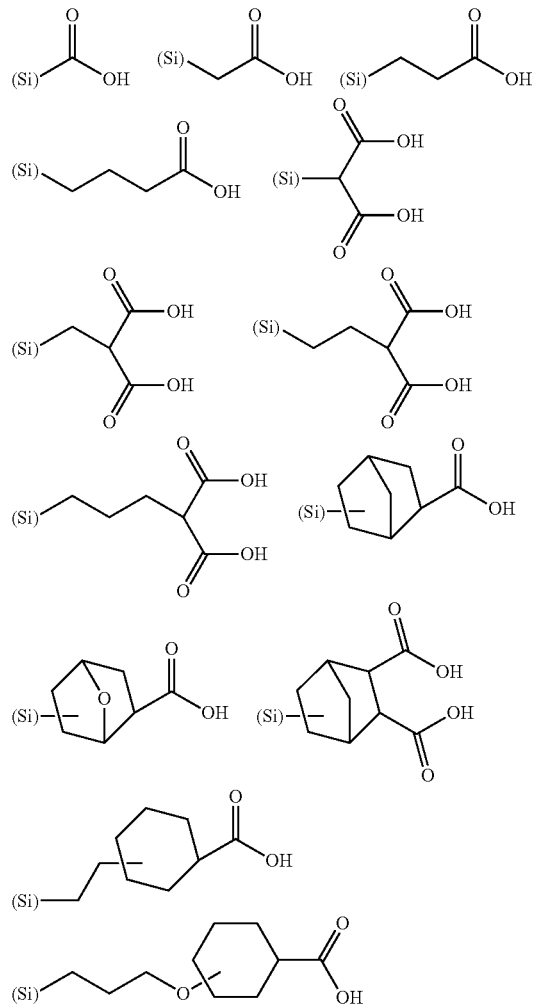

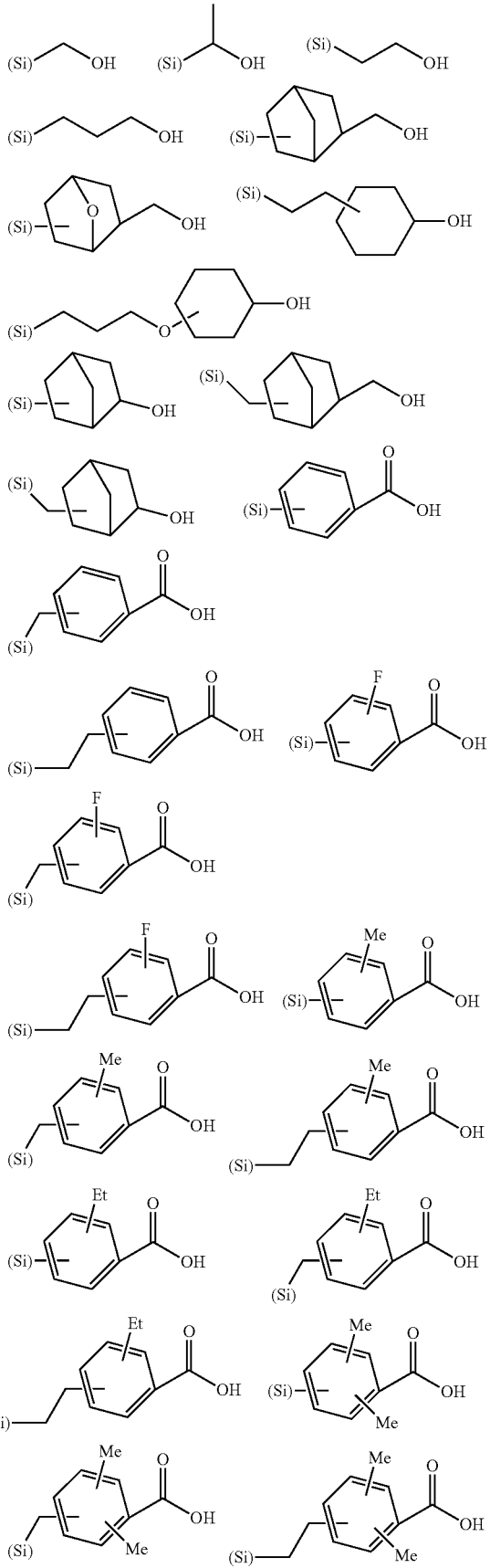

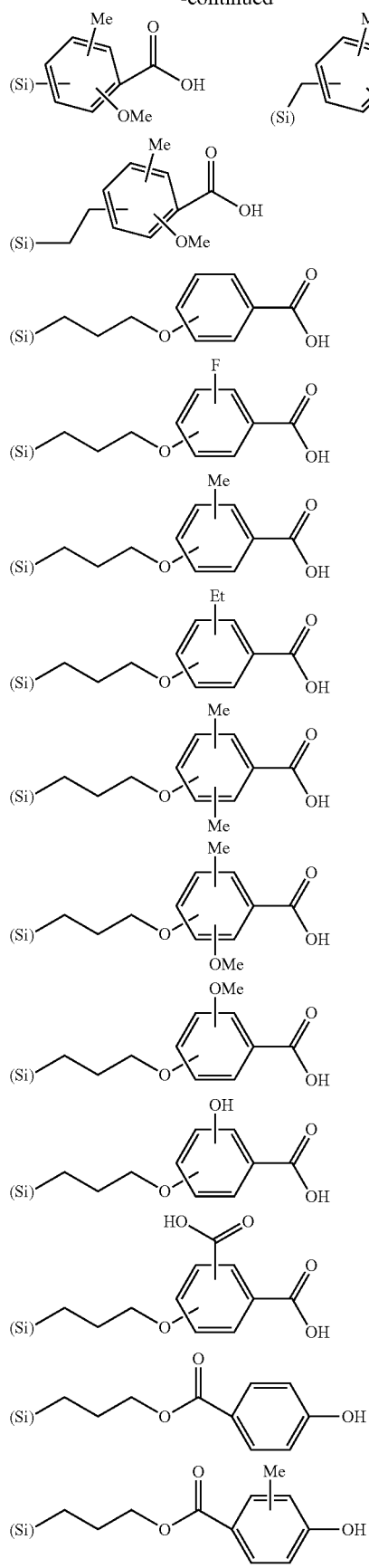
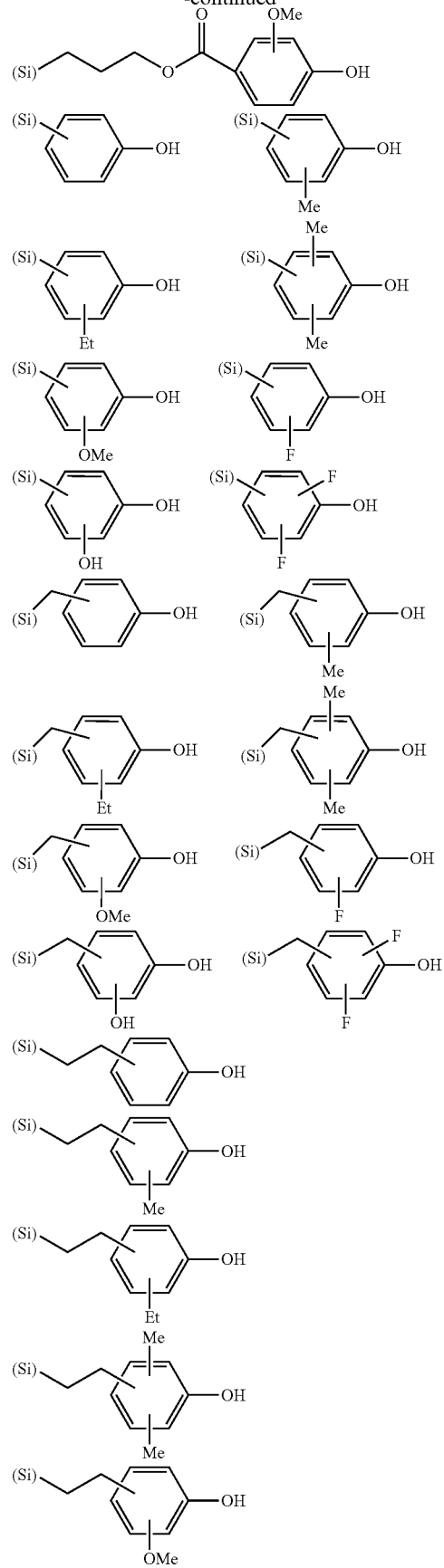

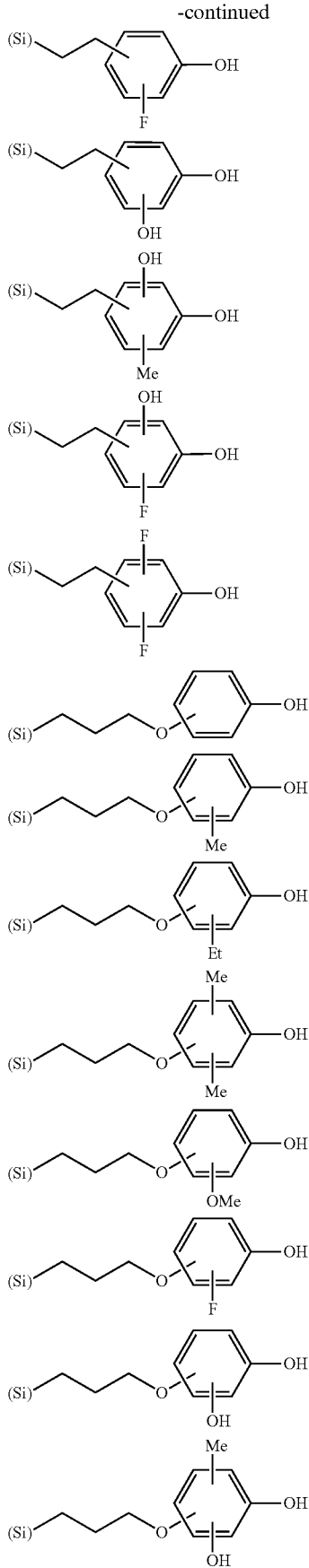
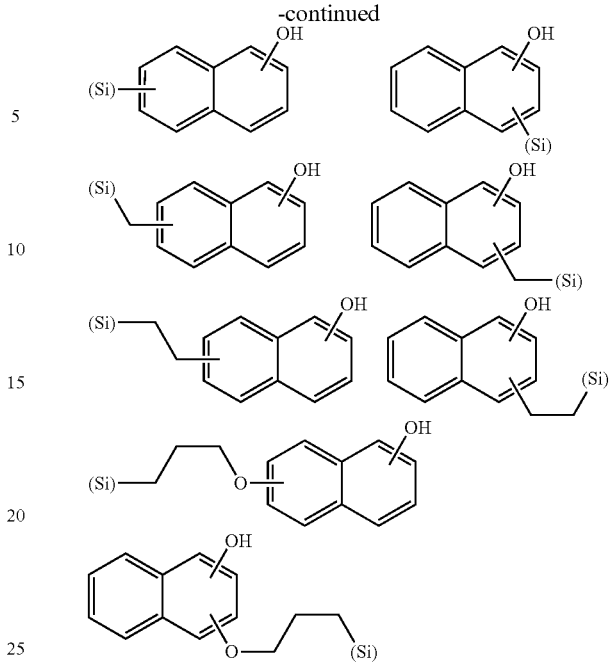

Examples of hydrolyzable monomers usable as starting materials for forming the silicon-containing surface modifier of the present invention include those each: having an applicable one of the above noted structures on a silicon atom; containing, as a hydrolyzable group, one, two, or three chlorine, bromine, iodine atoms, acetoxy groups, methoxy groups, ethoxy groups, propoxy groups, or butoxy groups; and containing, as each of $R^2$ and $R^3$, a hydrogen atom, or a monovalent organic group having 1 to 30 carbon atoms.

It is also possible to use such monomers where the above listed structures are each protected by a protective group at a hydroxyl group or carboxyl group thereof. In this case, such a protective group is not particularly limited insofar as the same can be deprotected during a production step of the silicon-containing surface modifier of the present invention, and, in case of exemplarily producing it by using an acid catalyst, it is possible to select such a monomer having a tertiary alkyl group or acetal group bonded thereto as a protective group. Contrary, it is possible to select an ester compound, in case of production by an alkali catalyst.

In addition, other hydrolyzable monomers shown below may be contained therein; and thus, the silicon-containing surface modifier of the present invention may be produced by hydrolytic condensation of a mixture like this.

Examples of other hydrolyzable monomers include: tetramethoxysilane, tetraethoxysilane, tetrapropoxysilane, tetraisopropoxysilane, trimethoxysilane, triethoxysilane, tripropoxysilane, triisopropoxysilane, methyltrimethoxysilane, methyltriethoxysilane, methyltripropoxysilane, methyltriisopropoxysilane, ethyltrimethoxysilane, ethyltriethoxysilane, ethyltripropoxysilane, ethyltriisopropoxysilane, vinyltrimethoxysilane, vinyltriethoxysilane, vinyltripropoxysilane, vinyltriisopropoxysilane, propyltrimethoxysilane, propyltriethoxysilane, propyltripropoxysilane, propyltriisopropoxysilane, isopropyltrimethoxysilane, isopropyltriethoxysilane, isopropyltripropoxysilane, isopropyltriisopropoxysilane, butyltrimethoxysilane, butyltriethoxysilane, butyltripropoxysilane, butyltriisopropoxysilane, sec-butyltrimethoxysilane, sec-butyltriethoxysilane, sec-butyltripropoxysilane, sec-butyltriisopropoxysilane, t-butyltrimethoxysilane, t-butyltriethoxysilane, t-butyltripropoxysilane, t-butyltriisopropoxysilane, cyclopropyltrimethoxysilane, cyclopropyltriethoxysilane, cyclopropyltripropoxysilane, cyclopropyltriisopropoxysilane, cyclobutyltrimethoxysilane, cyclobutyltriethoxysilane, cyclobutyltripropoxysilane, cyclobutyltriisopropoxysilane, cyclopentyltrimethoxysilane, cyclopentyltriethoxysilane, cyclopentyltripropoxysilane, cyclopentyltriisopropoxysilane, cyclohexyltrimethoxysilane, cyclohexyltriethoxysilane, cyclohexyltripropoxysilane, cyclohexyltriisopropoxysilane, cyclohexenyltrimethoxysilane, cyclohexenyltriethoxysilane, cyclohexenyltripropoxysilane, cyclohexenyltriisopropoxysilane, cyclohexenylethyltrimethoxysilane, cyclohexenylethyltriethoxysilane, cyclohexenylethyltripropoxysilane, cyclohexenylethyltriisopropoxysilane, cyclooctyltrimethoxysilane, cyclooctyltriethoxysilane, cyclooctyltripropoxysilane, cyclooctyltriisopropoxysilane, cyclopentadienylpropyltrimethoxysilane, cyclopentadienylpropyltriethoxysilane, cyclopentadienylpropyltripropoxysilane, cyclopentadienylpropyltriisopropoxysilane, bicycloheptenyltrimethoxysilane, bicycloheptenyltriethoxysilane, bicycloheptenyltripropoxysilane, bicycloheptenyltriisopropoxysilane, bicycloheptyltrimethoxysilane, bicycloheptyltriethoxysilane, bicycloheptyltripropoxysilane, bicycloheptyltriisopropoxysilane, adamantyltrimethoxysilane, adamantyltriethoxysilane, adamantyltripropoxysilane, adamantyltriisopropoxysilane, phenyltrimethoxysilane, phenyltriethoxysilane, phenyltripropoxysilane, phenyltriisopropoxysilane, benzyltrimethoxysilane, benzyltriethoxysilane, benzyltripropoxysilane, benzyltriisopropoxysilane, anisyltrimethoxysilane, anisyltriethoxysilane, anisyltripropoxysilane, anisyltriisopropoxysilane, tolyltrimethoxysilane, tolyltriethoxysilane, tolyltripropoxysilane, tolyltriisopropoxysilane, phenethyltrimethoxysilane, phenethyltriethoxysilane, phenethyltripropoxysilane, phenethyltriisopropoxysilane, naphthyltrimethoxysilane, naphthyltriethoxysilane, naphthyltripropoxysilane, naphthyltriisopropoxysilane, dimethyldimethoxysilane, dimethyldiethoxysilane, methylethyldimethoxysilane, methylethyldiethoxysilane, dimethyldipropoxysilane, dimethyldiisopropoxysilane, diethyldimethoxysilane, diethyldiethoxysilane, diethyldipropoxysilane, diethyldiisopropoxysilane, dipropyldimethoxysilane, dipropyldiethoxysilane, dipropyldipropoxysilane, dipropyldiisopropoxysilane, diisopropyldimethoxysilane, diisopropyldiethoxysilane, diisopropyldipropoxysilane, diisopropyldiisopropoxysilane, dibutyldimethoxysilane, dibutyldiethoxysilane, dibutyldipropoxysilane, dibutyldiisopropoxysilane, di-sec-butyldimethoxysilane, di-sec-butyldiethoxysilane, di-sec-butyldipropoxysilane, di-sec-butyldiisopropoxysilane, di-t-butyldimethoxysilane, di-t-butyldiethoxysilane, di-t-butyldipropoxysilane, di-t-butyldiisopropoxysilane, dicyclopropyldimethoxysilane, dicyclopropyldiethoxysilane, dicyclopropyldipropoxysilane, dicyclopropyldiisopropoxysilane, dicyclobutyldimethoxysilane, dicyclobutyldiethoxysilane, dicyclobutyldipropoxysilane, dicyclobutyldiisopropoxysilane, dicyclopentyldimethoxysilane, dicyclopentyldiethoxysilane, dicyclopentyldipropoxysilane, dicyclopentyldiisopropoxysilane, dicyclohexyldimethoxysilane, dicyclohexyldiethoxysilane, dicyclohexyldipropoxysilane, dicyclohexyldiisopropoxysilane, dicyclohexenyldimethoxysilane, dicyclohexenyldiethoxysilane, dicyclohexenyldipropoxysilane, dicyclohexenyldiisopropoxysilane, dicyclohexenylethyldimethoxysilane, dicyclohexenylethyldiethoxysilane, dicyclohexenylethyldipropoxysilane, dicyclohexenylethyldiisopropoxysilane, dicyclooctyldimethoxysilane, dicyclooctyldiethoxysilane, dicyclooctyldipropoxysilane, dicyclooctyldiisopropoxysilane, dicyclopentadienylpropyldimethoxysilane, dicyclopentadienylpropyldiethoxysilane, dicyclopentadienylpropyldipropoxysilane, dicyclopentadienylpropyldiisopropoxysilane, bis(bicycloheptenyl)dimethoxysilane, bis(bicycloheptenyl)diethoxysilane, bis(bicycloheptenyl)dipropoxysilane, bis(bicycloheptenyl)diisopropoxysilane, bis(bicycloheptyl)dimethoxysilane, bis(bicycloheptyl)diethoxysilane, bis(bicycloheptyl)dipropoxysilane, bis(bicycloheptyl)diisopropoxysilane, diadamantyldimethoxysilane, diadamantyldiethoxysilane, diadamantyldipropoxysilane, diadamantyldiisopropoxysilane, diphenyldimethoxysilane, diphenyldiethoxysilane, methylphenyldimethoxysilane, methylphenyldiethoxysilane, diphenyldipropoxysilane, diphenyldiisopropoxysilane, trimethylmethoxysilane, trimethylethoxysilane, dimethylethylmethoxysilane, dimethylethylethoxysilane, dimethylphenylmethoxysilane, dimethylphenylethoxysilane, dimethylbenzylmethoxysilane, dimethylbenzylethoxysilane, dimethylphenethylmethoxysilane, and dimethylphenethylethoxysilane.

Exemplarily preferable among the above listed other hydrolyzable monomers are: tetramethoxysilane, tetraethoxysilane, methyltrimethoxysilane, methyltriethoxysilane, ethyltrimethoxysilane, ethyltriethoxysilane, vinyltrimethoxysilane, vinyltriethoxysilane, propyltrimethoxysilane, propyltriethoxysilane, isopropyltrimethoxysilane, isopropyltriethoxysilane, butyltrimethoxysilane, butyltriethoxysilane, isobutyltrimethoxysilane, isobutyltriethoxysilane, allyltrimethoxysilane, allyltriethoxysilane, cyclopentyltrimethoxysilane, cyclopentyltriethoxysilane, cyclohexyltrimethoxysilane, cyclohexyltriethoxysilane, cyclohexenyltrimethoxysilane, cyclohexenyltriethoxysilane, phenyltrimethoxysilane, phenyltriethoxysilane, benzyltrimethoxysilane, benzyltriethoxysilane, tolyltrimethoxysilane, tolyltriethoxysilane, anisyltrimethoxysilane, anisyltriethoxysilane, phenethyltrimethoxysilane, phenethyltriethoxysilane, dimethyldimethoxysilane, dimethyldiethoxysilane, diethyldimethoxysilane, diethyldiethoxysilane, methylethyldimethoxysilane, methylethyldiethoxysilane, dipropyldimethoxysilane, dibutyldimethoxysilane, methylphenyldimethoxysilane, methylphenyldiethoxysilane, trimethylmethoxysilane, dimethylethylmethoxysilane, dimethylphenylmethoxysilane, dimethylbenzylmethoxysilane, and dimethylphenethylmethoxysilane.

When the $R^2$ and $R^3$ are each an organic group having 1 to 30 carbon atoms, examples of such an organic group include organic groups each having one or more carbon-oxygen single bonds, or carbon-oxygen double bonds. Specifically, such organic groups are each to have one or more groups selected from a group consisting of an epoxy group, an ester group, an alkoxy group, and a hydroxy group. Examples of such organic groups include those each represented by the following general formula (1):

$$(P-Q_1-(S_1)_{v1}-Q_2-)_u-(T)_{v2}-Q_3-(S_2)_{v3}-Q_4-$$ (1)

wherein

P represents a hydrogen atom, a hydroxyl group, a epoxy ring

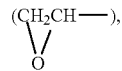

an alkoxy group having 1 to 4 carbon atoms, an alkylcarbonyloxy group having 1 to 6 carbon atoms, or an alkylcarbonyl group having 1 to 6 carbon atoms;

$Q_1$, $Q_2$, $Q_3$, and $Q_4$ are each independently $-C_qH_{(2q-p)}P_p-$ (in the formula, P represents the same as the above, p represents an integer of 0 to 3, and q represents an integer of 0 to 10 (where q=0 means a single bond);

u represents an integer of 0 to 3;

$S_1$ and $S_2$ each independently represent —O—, —CO—, —OCO—, —COO—, or —OCOO—;

v1, v2, and v3 each independently represent 0 or 1;

simultaneously with the above, T represents a divalent group comprising an alicycle or aromatic ring which may include a hetero atom, and examples of the alicycle or aromatic ring as T which may include a hetero atom such as an oxygen atom are described below; and the group T is not particularly limited in terms of sites to be bonded to $Q_2$ and $Q_3$, respectively, and such sites are appropriately selectable in view of the reactivity depending on a steric factor, availability of a commercial reagent to be used for the reaction, and the like.

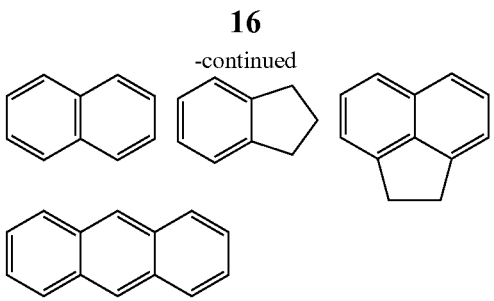

Preferable examples of the organic groups each having one or more carbon-oxygen single bonds, or carbon-oxygen double bonds and each represented by the above general formula (1), include the following. The following formulae each include a mark (Si) so as to show a bonding site to Si.

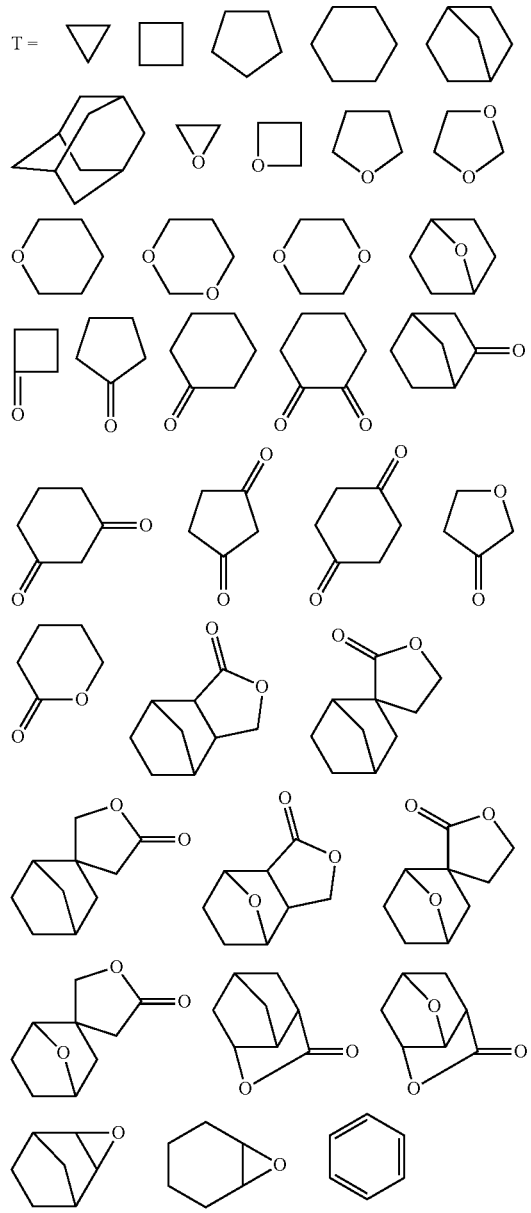

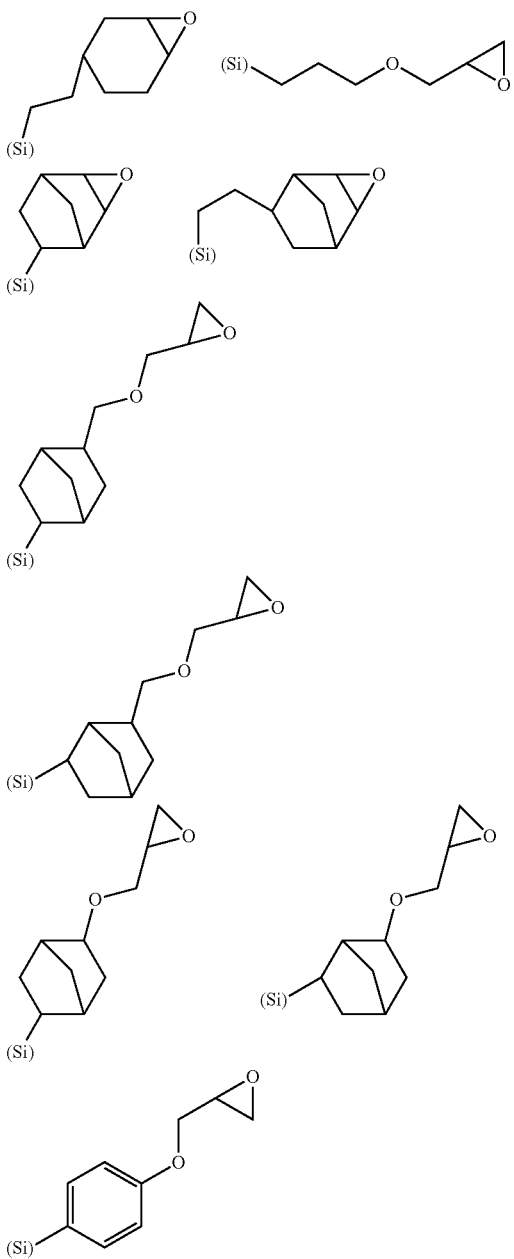

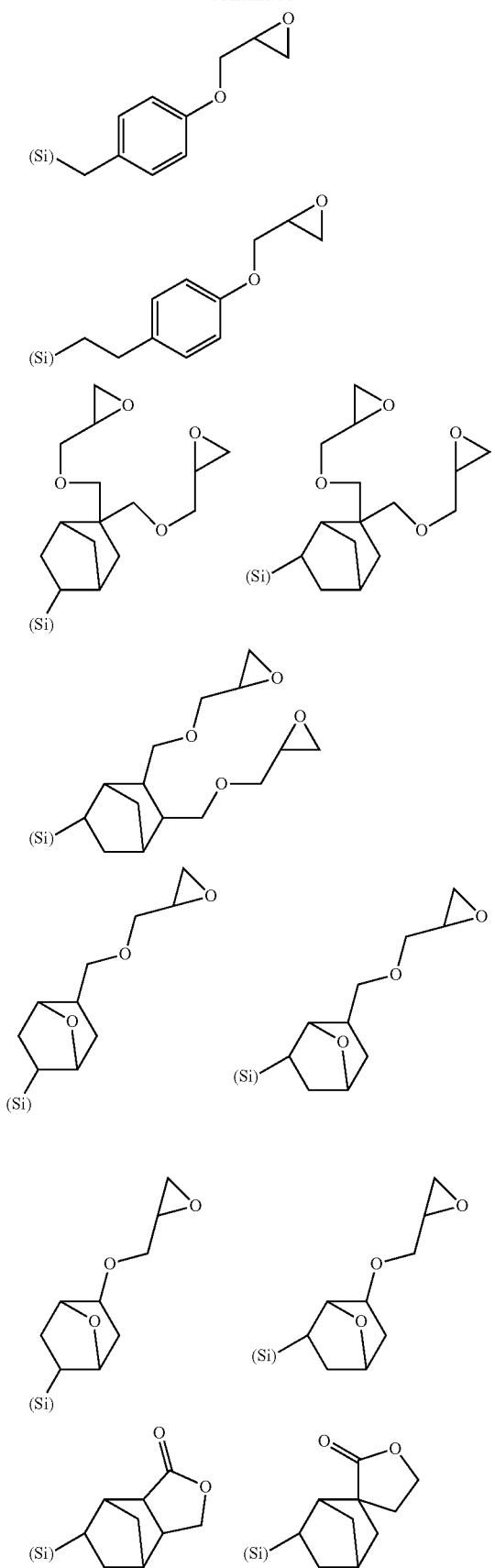
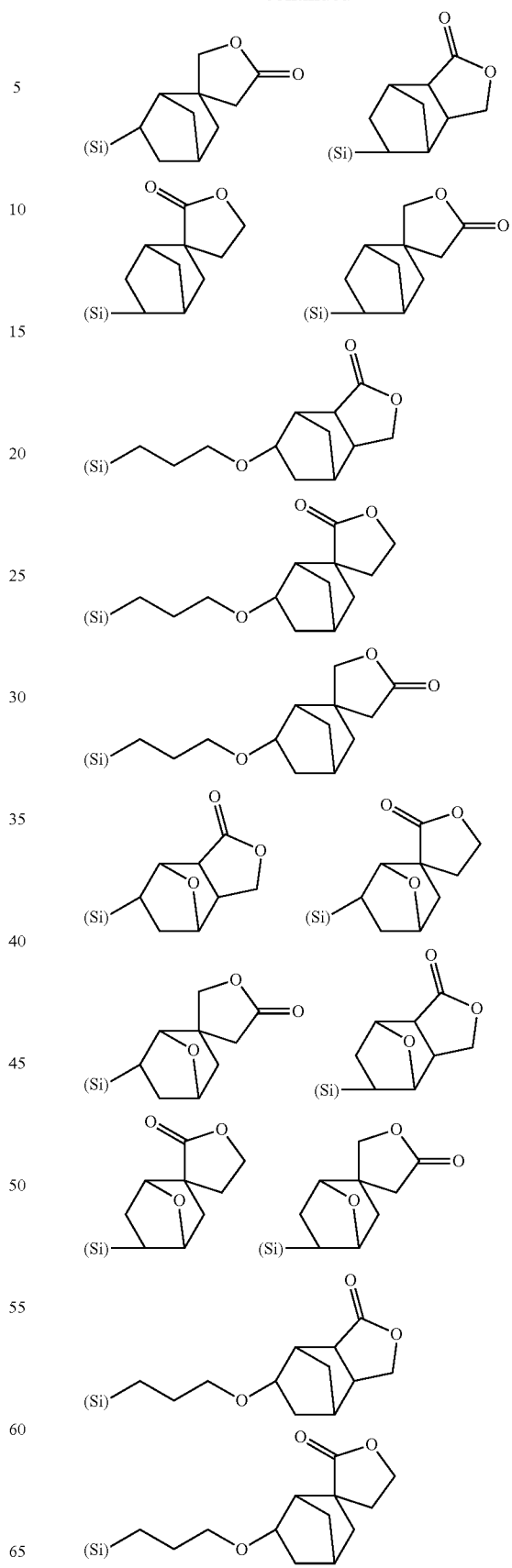

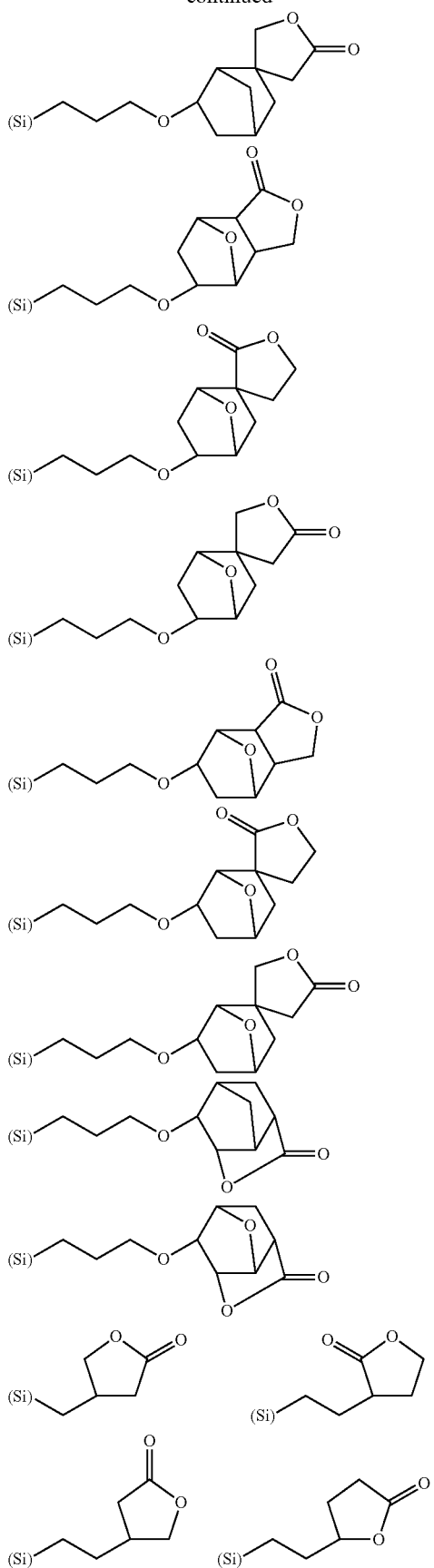
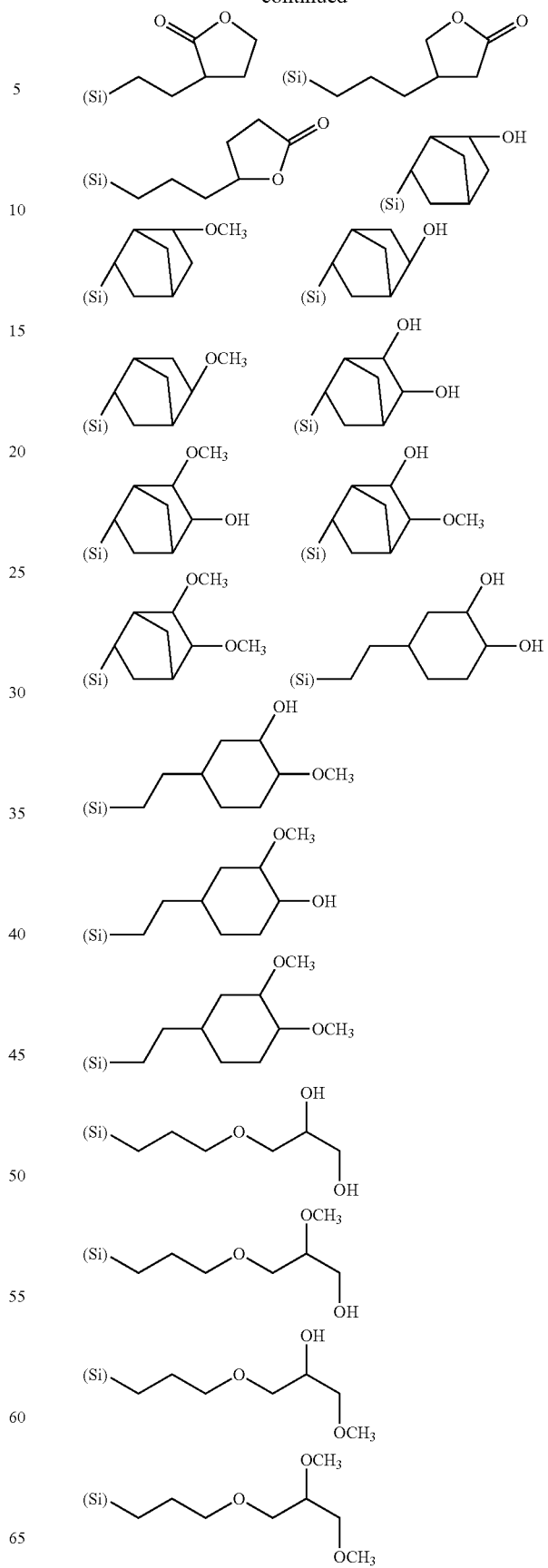

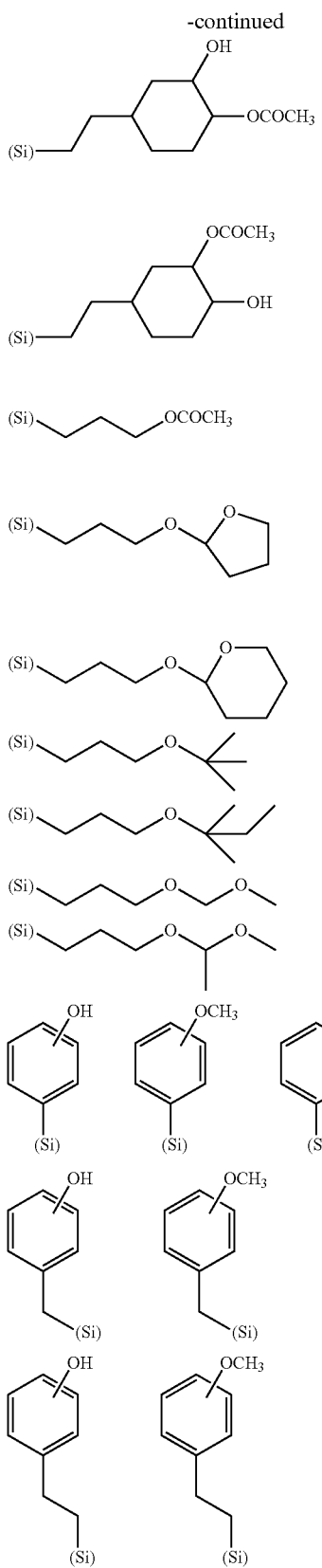

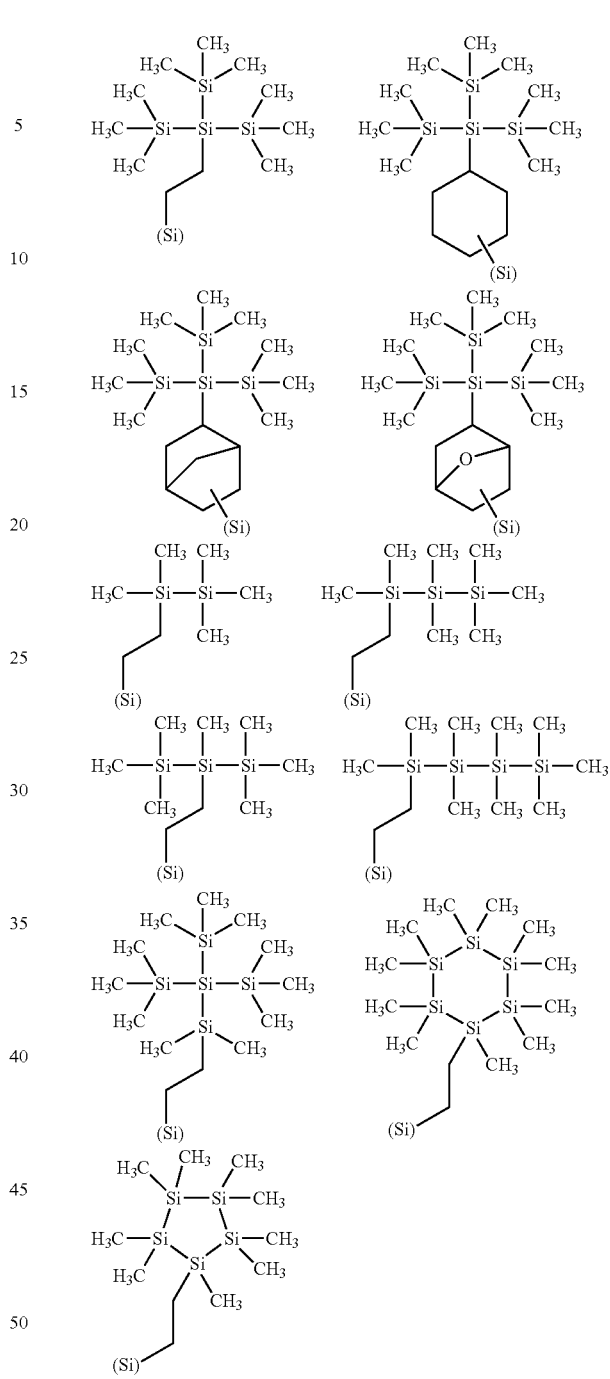

As exemplary organic groups as $R^2$ and $R^3$, it is also possible to use organic groups each including a silicon-silicon bond. Specific examples thereof include the following:

[Synthesizing Method of Silicon-Containing Surface Modifier]

(Synthesizing Method 1: Acid Catalyst)

The silicon-containing surface modifier of the present invention can be produced by hydrolytic condensation of a mixture of one kind or two or more kinds of the above-mentioned hydrolyzable monomers, in the presence of an acid catalyst, for example.

Examples of the acid catalyst to be used then include: organic acids such as formic acid, acetic acid, oxalic acid, and maleic acid; a hydrofluoric acid; a hydrochloric acid; a hydrobromic acid; a sulfuric acid; a nitric acid; a perchloric acid; a phosphoric acid; a methanesulfonic acid; a benzenesulfonic acid; a toluenesulfonic acid; and the like. The usage amount of the catalyst is to be $1\times10^{-6}$ to 10 moles, preferably $1\times10^{-5}$ to 5 moles, and more preferably $1\times10^{-1}$ to 1 mole, relative to 1 mole of monomers.

The amount of water to be added upon obtainment of a silicon-containing surface modifier from these monomers is 0.01 to 100 moles, preferably 0.05 to 50 moles, and more preferably 0.1 to 30 moles, relative to 1 mole of hydrolyzable substitutional groups bonded to the monomers. Addition amounts of 100 moles or less of water economically lead to smaller apparatuses to be used for the reaction.

As a manipulation manner, the monomers are added into a catalyst water solution, thereby initiating a hydrolytic condensation reaction. At this time, it is possible to add an organic solvent into the catalyst water solution, or to previously dilute the monomers with an organic solvent, or to conduct both the manipulations. The reaction temperature is to be between 0 and 100° C., and preferably between 5 and 80° C. It is a preferable manner to keep the temperature between 5 and 80° C. upon dropping of the monomers, and to subsequently conduct maturation at a temperature between 20 and 80° C.

Preferable examples of the organic solvent which can be added to the catalyst water solution or which can dilute the monomers include: methanol, ethanol, 1-propanol, 2-propanol, 1-butanol, 2-butanol, 2-methyl-1-propanol, acetone, acetonitrile, tetrahydrofuran, toluene, hexane, ethyl acetate, acetone, methyl ethyl ketone, methyl isobutyl ketone, cyclohexanone, methyl amyl ketone, butanediol monomethyl ether, propyleneglycol monomethyl ether, ethyleneglycol monomethyl ether, butanediol monoethyl ether, propyleneglycol monoethyl ether, ethyleneglycol monoethyl ether, propyleneglycol dimethyl ether, diethyleneglycol dimethyl ether, propyleneglycol monomethyl ether acetate, propyleneglycol monoethyl ether acetate, ethyl pyruvate, butyl acetate, methyl 3-methoxypropionate, ethyl 3-ethoxypropionate, tert-butyl acetate, t-butyl propionate, propyleneglycol mono-t-butyl ether acetate, γ-butyrolactone, acetonitrile, tetrahydrofuran, and a mixture thereof.

Among the solvents, water-soluble ones are preferable. Examples thereof include: alcohols such as methanol, ethanol, 1-propanol, and 2-propanol; polyhydric alcohols such as ethylene glycol, and propylene glycol; polyhydric alcohol condensation derivatives such as butane diol monomethyl ether, propylene glycol monomethyl ether, ethylene glycol monomethyl ether, butane diol monoethyl ether, propylene glycol monoethyl ether, ethylene glycol monoethyl ether, butane diol monopropyl ether, propylene glycol monopropyl ether, ethylene glycol monopropyl ether; acetone; acetonitrile; tetrahydrofuran; and the like. Particularly preferable among them are those each having a boiling point of 100° C. or lower.

The usage amount of the organic solvent is to be 0 to 1,000 ml, preferably 0 to 500 ml, relative to 1 mole of monomers. Smaller usage amounts of the organic solvent economically lead to smaller reaction vessels.

To be subsequently obtained is a reaction mixture water solution, while conducting a neutralization reaction for the catalyst if required. At this time, the amount of an alkaline substance usable for the neutralization is to be preferably 0.1 to 2 equivalents relative to the acid used as the catalyst. This alkaline substance may be an arbitrary one, insofar as the same exhibits an alkalinity in water.

Subsequently, it is preferable to remove, from the reaction mixture, by-products such as alcohols produced by the hydrolytic condensation reaction, by removal under reduced pressure, for example. Although the temperature to which the reaction mixture is heated at this time depends on the type of the added organic solvent, the types of alcohols produced by the reaction, and the like, the temperature is to be preferably between 0 and 100° C., more preferably between 10 and 90° C., and most preferably between 15 and 80° C. Further, although the reduced pressure degree is varied depending on the types of the organic solvent, alcohols, and the like to be removed, an exhaust device, a condensation device, and the heating temperature, the reduced pressure degree is to be preferably at an atmospheric pressure or lower, more preferably 80 kPa or lower as an absolute pressure, and most preferably 50 kPa or lower as an absolute pressure. Although it is difficult to precisely identify an amount of alcohols removed at this time, it is desirable to remove 80 mass % or more of the produced alcohols and the like.

Next, it is possible to remove, from the reaction mixture, the acid catalyst used for the hydrolytic condensation. As a technique to remove the acid catalyst, the silicon-containing surface modifier is to be mixed with water, and the silicon-containing surface modifier is then extracted from the mixture by an organic solvent. Preferable as the organic solvent to be used then, is one capable of dissolving the silicon-containing surface modifier therein and capable of being separated in a two-layer manner from water when mixed therewith. Examples of such an organic solvent include methanol, ethanol, 1-propanol, 2-propanol, 1-butanol, 2-butanol, 2-methyl-1-propanol, acetone, tetrahydrofuran, toluene, hexane, ethyl acetate, acetone, cyclohexanone, methyl amyl ketone, butanediol monomethyl ether, propyleneglycol monomethyl ether, ethyleneglycol monomethyl ether, butanediol monoethyl ether, propyleneglycol monoethyl ether, ethyleneglycol monoethyl ether, butanediol monopropyl ether, propyleneglycol monopropyl ether, ethyleneglycol monopropyl ether, propyleneglycol dimethyl ether, diethyleneglycol dimethyl ether, propyleneglycol monomethyl ether acetate, propyleneglycol monoethyl ether acetate, ethyl pyruvate, butyl acetate, methyl 3-methoxypropionate, ethyl 3-ethoxypropionate, t-butyl acetate, t-butyl propionate, propyleneglycol mono-t-butyl ether acetate, γ-butyrolactone, methyl isobutyl ketone, cyclopentyl methyl ether, tetrahydrofuran, and a mixture thereof.

It is also possible to use a mixture of a water-soluble organic solvent and a poorly water-soluble organic solvent. Preferable examples of the mixture include: methanol/ethyl acetate mixture, ethanol/ethyl acetate mixture, 1-propanol/ethyl acetate mixture, 2-propanol/ethyl acetate mixture, butane diol monomethyl ether/ethyl acetate mixture, propylene glycol monomethyl ether/ethyl acetate mixture, ethylene glycol monomethyl ether/ethyl acetate mixture, butane diol monoethyl ether/ethyl acetate mixture, propylene glycol monoethyl ether/ethyl acetate mixture, ethylene glycol monoethyl ether/ethyl acetate mixture, butane diol monopropyl ether/ethyl acetate mixture, propylene glycol monopropyl ether/ethyl acetate mixture, ethylene glycol monopropyl ether/ethyl acetate mixture, methanol/methyl isobutyl ketone mixture, ethanol/methyl isobutyl ketone mixture, 1-propanol/methyl isobutyl ketone mixture, 2-propanol/methyl isobutyl ketone mixture, propylene glycol monomethyl ether/methyl isobutyl ketone mixture, ethylene glycol monomethyl ether/methyl isobutyl ketone mixture, propylene glycol monoethyl ether/methyl isobutyl ketone mixture, ethylene glycol monoethyl ether/methyl isobutyl ketone mixture, propylene glycol monopropyl ether/methyl isobutyl ketone mixture, ethylene glycol monopropyl ether/methyl isobutyl ketone mixture, methanol/cyclopentyl methyl ether mixture, ethanol/cyclopentyl methyl ether mixture, 1-propanol/cyclopentyl methyl ether mixture, 2-propanol/cyclopentyl methyl ether mixture, propylene glycol monomethyl ether/cyclopentyl methyl ether mixture, ethylene glycol monomethyl ether/cyclopentyl methyl ether mixture, propylene glycol monoethyl ether/cyclopentyl methyl ether mixture, ethylene glycol monoethyl ether/cyclopentyl methyl ether mixture, propylene glycol monopropyl ether/cyclopentyl methyl ether mixture, ethylene glycol monopropyl ether/cyclopentyl methyl ether mixture, methanol/propylene glycol methyl ether acetate mixture, ethanol/propylene glycol methyl ether acetate mixture, 1-propanol/propylene glycol methyl ether acetate mixture, 2-propanol/propylene glycol methyl ether acetate mixture, propylene glycol monomethyl ether/propylene glycol methyl ether acetate mixture, ethylene glycol monomethyl ether/propylene glycol methyl ether acetate mixture, propylene glycol monoethyl ether/propylene glycol methyl ether acetate mixture, ethylene glycol monoethyl ether/propylene glycol methyl ether acetate mixture, propylene glycol monopropyl ether/propylene glycol methyl ether acetate mixture, ethylene glycol monopropyl ether/propylene glycol methyl ether acetate mixture; and the like; without limited to these combinations.

Although the mixing ratio of the water-soluble organic solvent and the poorly water-soluble organic solvent is to be appropriately selected, it is desirable to use the water-soluble organic solvent in an amount between 0.1 and 1,000 parts by mass, preferably between 1 and 500 parts by mass, and more preferably between 2 and 100 parts by mass, relative to 100 parts by mass of the poorly water-soluble organic solvent.

Subsequently, the resultant reaction mixture may be washed by neutral water. This water is typically called a deionized water or ultrapure water. The amount of this water is to be between 0.01 and 100 L, preferably between 0.05 and SOL, and more preferably between 0.1 and 5 L, relative to 1 L of the silicon-containing surface modifier solution. The manner of washing may be configured to introduce both the solution and the water into the same vessel, to stir them, to subsequently leave them to stand still, and to separate a water layer therefrom. Although one or more times of washing are enough, such a number of times is to be preferably one to five because a commensurate washing effect is not obtained even when ten or more times of washing are conducted.

Examples of other techniques to remove the acid catalyst include: a technique using an ion-exchange resin; a technique to neutralize the acid catalyst with an epoxy compound such as ethylene oxide, propylene oxide, or the like followed by removal; and the like. These techniques can be appropriately selected depending on the acid catalyst used for the reaction.

Since the water washing operation at this time may sometimes bring about an effect substantially equivalent to a fractionation operation because part of the silicon-containing surface modifier is caused to get into the water layer, the number of washing times and the amount of washing water are to be appropriately selected in view of a balance between the catalyst removing effect and the fractionating effect.

In either case of the silicon-containing surface modifier solution containing the residual acid catalyst or the silicon-containing surface modifier solution from which the acid catalyst has been removed, the solution is subjected to addition of a final solvent in a manner to conduct solvent exchange under reduced pressure, thereby obtaining a desired silicon-containing surface modifier solution. Although depending on the types of the reaction solvent and the extraction solvent both to be removed, the temperature of solvent exchange is to be preferably between 0 and 100° C., more preferably between 10 and 90° C., and most preferably between 15 and 80° C. Further, although the reduced pressure degree is varied depending on the type of the extraction solvent to be removed, an exhaust device, a condensation device, and the heating temperature, the reduced pressure degree is to be preferably at an atmospheric pressure or lower, more preferably 80 kPa or lower as an absolute pressure, and most preferably 50 kPa or lower as an absolute pressure.

At this time, the silicon-containing surface modifier is occasionally made to be unstable, due to solvent exchange. This phenomenon is caused depending on the compatibility between the final solvent and the silicon-containing surface modifier, and it is possible to add a monohydric, dihydric, or higher alcohol having a cyclic ether as a substitutional group described at paragraphs (0181) to (0182) of JP2009-126940A, as a stabilizer. The addition amount of such an alcohol is to be between 0 and 25 parts by mass, preferably between 0 and 15 parts by mass, and more preferably between 0 and 5 parts by mass, relative to 100 parts by mass of the silicon-containing surface modifier in the solution before solvent exchange, and the amount when added is to be preferably 0.5 parts by mass or more. If necessary, the solvent exchange operation is to be conducted such that the monohydric, dihydric, or higher alcohol having a cyclic ether as a substitutional group is added before solvent exchange.

When the silicon-containing surface modifier is concentrated to a certain concentration or thicker, the condensation reaction is further progressed such that the modifier is possibly turned into a state which is unable to be again dissolved in the organic solvent. Thus, the modifier is to be preferably kept in a solution state at an appropriate concentration. Also, excessively thinner concentrations lead to excessively larger amounts of the solvent, so that the modifier is to be economically preferably kept in a solution state at an appropriate concentration. The concentration at this time is to be preferably between 0.1 and 20 mass %.

Preferable as the final solvent to be added into the silicon-containing surface modifier solution is an alcohol-based solvent, and particularly preferable are monoalkyl ether derivatives of ethylene glycol, diethylene glycol, triethylene glycol, propylene glycol, dipropylene glycol, butanediol, and the like. Specifically preferable are butane diol monomethyl ether, propylene glycol monomethyl ether, ethylene glycol monomethyl ether, butane diol monoethyl ether, propylene glycol monoethyl ether, ethylene glycol monoethyl ether, butane diol monopropyl ether, propylene glycol monopropyl ether, ethylene glycol monopropyl ether, and the like.

When these solvents are main components, it is also possible to add a non-alcoholic solvent as a cosolvent. Examples of the cosolvent include acetone, tetrahydrofurane, toluene, hexane, ethyl acetate, cyclohexanone, methyl amyl ketone, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxypropionate, ethyl 3-ethoxypropionate, t-butyl acetate, t-butyl propionate, propylene glycol mono-t-butyl ether acetate, γ-butyrolactone, methyl isobutyl ketone, cyclopentyl methyl ether, and the like.

As another operation for reaction upon adoption of the acid catalyst, water or a water-containing organic solvent is to be added to the monomers or into an organic solution of monomers, to initiate a hydrolysis reaction. At this time, the catalyst may be added to the monomers or into the organic solution of monomers, or may have been added into water or the water-containing organic solvent. The reaction temperature is to be between 0 and 100° C., preferably between 10 and 80° C. It is a preferable manner to heat up to 10 to 50° C. upon dropping of water, and to thereafter elevate the temperature up to 20 to 80° C., thereby conducting maturation.

In case of using the organic solvent, water-soluble ones are preferable, and examples thereof include: methanol, ethanol, 1-propanol, 2-propanol, 1-butanol, 2-butanol, 2-methyl-1-propanol, acetone, tetrahydrofuran, acetonitrile; polyhydric alcohol condensation derivatives such as butane diol monomethyl ether, propylene glycol monomethyl ether, ethylene glycol monomethyl ether, butane diol monoethyl ether, propylene glycol monoethyl ether, ethylene glycol monoethyl ether, butane diol monopropyl ether, propylene glycol monopropyl ether, ethylene glycol monopropyl ether, propylene glycol dimethyl ether, diethylene glycol dimethyl ether, propylene glycol monomethyl ether acetate, propylene glycol monoethyl ether acetate, propylene glycol monopropyl ether, and the like; and mixtures thereof.

The usage amount of the organic solvent is to be 0 to 1,000 ml, preferably 0 to 500 ml, relative to 1 mole of monomers. Smaller usage amounts of the organic solvent economically lead to smaller reaction vessels. The obtained reaction mixture is to be subjected to a post treatment in the same manner as the above, thereby enabling to obtain a silicon-containing surface modifier.

(Synthesizing Method 2: Alkali Catalyst)

The silicon-containing surface modifier of the present invention can also be produced by hydrolytic condensation of a mixture of one kind or two or more kinds of the above-mentioned hydrolyzable monomers, in the presence of an alkali catalyst, for example.

Examples of the alkali catalyst to be used then include: methylamine, ethylamine, propylamine, butylamine, ethylenediamine, hexamethylenediamine, dimethylamine, diethylamine, ethylmethylamine, trimethylamine, triethylamine, tripropylamine, tributylamine, cyclohexylamine, dicyclohexylamine, monoethanolamine, diethanolamine, dimethylmonoethanolamine, monomethyldiethanolamine, triethanolamine, diazabicyclooctane, diazabicyclocyclononene, diazabicycloundecene, hexamethylenetetramine, aniline, N,N-dimethylaniline, pyridine, N,N-dimethylaminopyridine, pyrrole, piperazine, pyrrolidine, piperidine, picoline, tetramethylammonium hydroxide, choline hydroxide, tetrapropylammonium hydroxide, tetrabutylammonium hydroxide, ammonia, lithium hydroxide, sodium hydroxide, potassium hydroxide, barium hydroxide, calcium hydroxide, and the like. The usage amount of the catalyst is to be $1\times10^{-6}$ to 10 moles, preferably $1\times10^{-5}$ to 5 moles, and more preferably $1\times10^{-4}$ to 1 mole, relative to 1 mole of silicon monomers.

The amount of water to obtain the silicon-containing surface modifier by hydrolytic condensation reaction of the foregoing monomers is preferably 0.1 to 50 moles, relative to 1 mole of the hydrolysable substituent groups bonded to the monomers. Addition amounts of 50 moles or less of water economically lead to smaller apparatuses to be used for the reaction.

As a manipulation manner, the monomers are added into a catalyst water solution, thereby initiating a hydrolytic condensation reaction. At this time, it is possible to add an organic solvent into the catalyst water solution, or to previously dilute the monomers with an organic solvent, or to conduct both the manipulations. The reaction temperature is to be between 0 and 100° C., and preferably between 5 and 80° C. It is a preferable manner to keep the temperature between 5 and 80° C. upon dropping of the monomers, and to subsequently conduct maturation at a temperature between 20 and 80° C.

Preferably usable examples of the organic solvent which can be added to the catalyst water solution or which can dilute the monomers, are the same as those organic solvents exemplified to be allowed to be added into the acid catalyst water solution. The usage amount of the organic solvent is to be preferably between 0 and 1,000 ml relative to 1 mole of monomers, so as to economically conduct the reaction.

To be subsequently obtained is a reaction mixture water solution, while conducting a neutralization reaction for the catalyst if required. At this time, the amount of an acidic substance usable for the neutralization is to be preferably 0.1 to 2 equivalents relative to the alkaline substance used as the catalyst. This acidic substance may be an arbitrary one, insofar as the same exhibits an acidity in water.

Subsequently, it is preferable to remove, from the reaction mixture, by-products such as alcohols produced by the hydrolytic condensation reaction, by removal under reduced pressure, for example. Although the temperature to which the reaction mixture is heated depends on the type of the added organic solvent, the types of alcohols produced by the reaction, and the like, the temperature is to be preferably between 0 and 100° C., more preferably between 10 and 90° C., and most preferably between 15 and 80° C. Further, although the reduced pressure degree is varied depending on the types of the organic solvent, alcohols, and the like to be removed, an exhaust device, a condensation device, and the heating temperature, the reduced pressure degree is to be preferably at an atmospheric pressure or lower, more preferably 80 kPa or lower as an absolute pressure, and most preferably 50 kPa or lower as an absolute pressure. Although it is difficult to precisely identify an amount of alcohols removed at this time, it is desirable to remove 80 mass % or more of the produced alcohols and the like.

Next, the silicon-containing surface modifier is extracted by an organic solvent, so as to remove the alkali catalyst used for the hydrolytic condensation. Preferable as the organic solvent to be used then, is one capable of dissolving the silicon-containing surface modifier therein and capable of being separated in a two-layer manner from water when mixed therewith. It is also possible to use a mixture of a water-soluble organic solvent and a poorly water-soluble organic solvent.

Specific usable examples of the organic solvent to be used upon removal of the alkali catalyst are the same as those organic solvents, and those mixtures of water-soluble organic solvent and poorly water-soluble organic solvent which have been specifically enumerated above to be used upon removal of the acid catalyst.

Although the mixing ratio of the water-soluble organic solvent and the poorly water-soluble organic solvent is to be appropriately selected, it is desirable to use the water-soluble organic solvent in an amount between 0.1 and 1,000 parts by mass, preferably between 1 and 500 parts by mass, and more preferably between 2 and 100 parts by mass, relative to 100 parts by mass of the poorly water-soluble organic solvent.

Subsequently, the silicon-containing surface modifier solution is to be washed by neutral water. This water is typically called a deionized water or ultrapure water. The amount of this water is to be between 0.01 and 100 L, preferably between 0.05 and 50 L, and more preferably between 0.1 and 5 L, relative to 1 L of the silicon-containing surface modifier solution. The manner of washing may be configured to introduce both the solution and the water into the same vessel, to stir them, to subsequently leave them to stand still, and to separate a water layer therefrom. Although one or more times of washing are enough, such a number of times is to be preferably one to five because a commensurate washing effect is not obtained even when ten or more times of washing are conducted.

The silicon-containing surface modifier solution having been washed is to be subjected to addition of a final solvent in a manner to conduct solvent exchange under reduced pressure, thereby obtaining a desired silicon-containing surface modifier solution. Although depending on the types of the extraction solvent to be removed, the temperature of solvent exchange is to be preferably between 0 and 100° C., more preferably between 10 and 90° C., and most preferably between 15 and 80° C. Further, although the reduced pressure degree is varied depending on the type of the extraction solvent to be removed, an exhaust device, a condensation device, and the heating temperature, the reduced pressure degree is to be preferably at an atmospheric pressure or lower, more preferably 80 kPa or lower as an absolute pressure, and most preferably 50 kPa or lower as an absolute pressure.

Preferable as the final solvent to be added into the silicon-containing surface modifier solution is an alcoholic solvent, and particularly preferable are monoalkyl ethers of ethylene glycol, diethylene glycol, triethylene glycol, and the like, and monoalkyl ethers of propylene glycol, dipropylene glycol, and the like. Specifically preferable are propylene glycol monomethyl ether, ethylene glycol monomethyl ether, propylene glycol monoethyl ether, ethylene glycol monoethyl ether, propylene glycol monopropyl ether, ethylene glycol monopropyl ether, and the like.

As another operation for reaction upon adoption of the alkali catalyst, water or a water-containing organic solvent is to be added to the monomers or into an organic solution of monomers, to initiate a hydrolysis reaction. At this time, the catalyst may be added to the monomers or into the organic solution of monomers, or may have been added into water or the water-containing organic solvent. The reaction temperature is to be between 0 and 100° C., preferably between 10 and 80° C. It is a preferable manner to heat up to 10 to 50° C. upon dropping of water, and to thereafter elevate the temperature up to 20 to 80° C., thereby conducting maturation.

The organic solvent usable as the organic solvent for monomers or as the water-containing organic solvent is preferably a water-soluble one, and examples thereof include: methanol, ethanol, 1-propanol, 2-propanol, 1-butanol, 2-butanol, 2-methyl-1-propanol, acetone, tetrahydrofuran, acetonitrile; polyhydric alcohol condensation derivatives such as propylene glycol monomethyl ether, ethylene glycol monomethyl ether, propylene glycol monoethyl ether, ethylene glycol monoethyl ether, propylene glycol monopropyl ether, ethylene glycol monopropyl ether, propylene glycol dimethyl ether, diethylene glycol dimethyl ether, propylene glycol monomethyl ether acetate, propylene glycol monoethyl ether acetate, propylene glycol monopropyl ether, and the like; and mixtures thereof.

Although the silicon-containing surface modifiers obtained by the synthetic methods 1 and 2 can each be adjusted in molecular weight, not only by selection of monomers but also by control of a reaction condition upon polymerization, it is preferable to use such a silicon-containing surface modifier having a molecular weight of 100,000 or less, preferably between 200 and 50,000, more preferably between 300 and 30,000. Weight-average molecular weights of 100,000 or less never cause occurrence of foreign matters, coating irregularities, and the like.

It is noted that the data concerning the weight-average molecular weights are represented as molecular weights determined relative to polystyrenes used as standard substances, respectively, based on a gel permeation chromatography (GPC) using RI as a detector and tetrahydrofuran as an eluting solvent.

Meanwhile, the present invention provides a silicon-containing resist lower layer film-forming composition containing such a silicon-containing surface modifier, and a polysiloxane compound.

The blending amount of the silicon-containing surface modifier is to be between 0.01 and 50, preferably between 0.1 and 10, in mass ratio, assuming the polysiloxane compound as a base polymer to be 100.

The polysiloxane compound to be contained in the resist lower layer film-forming composition produced by using the silicon-containing surface modifier of the present invention, can be produced under a condition using the other hydrolyzable monomers and the acid catalyst or alkali catalyst as noted above.

Further, it is possible to use, as a component of the resist lower layer film-forming composition, the polysiloxane derivative produced under a condition using a mixture of such a monomer and a hydrolyzable metal compound represented by the following general formula (2), as well as the acid catalyst or alkali catalyst as noted above, $$U(OR^7)_{m7}(OR^8)_{m8} \quad (2)$$

wherein
$R^7$ and $R^8$ represent each an organic group having 1 to 30 carbon atoms;
m7+m8 represents the same number as a valence to be determined by a kind of U;
m7 and m8 represent each an integer of 0 or greater; and
U represents an element belonging to group III, group IV or group V of the periodic table, except for carbon and silicon.

Examples of the hydrolyzable metal compound (2) usable at this time include the following. In case that U is boron, examples of the compound represented by the general formula (2) include monomers such as boron methoxide, boron ethoxide, boron propoxide, boron butoxide, boron amyloxide, boron hexyloxide, boron cyclopentoxide, boron cyclohexyloxide, boron allyloxide, boron phenoxide, boron methoxyethoxide, boric acid, boron oxide, and the like.

In case that U is aluminum, examples of the compound represented by the general formula (2) include monomers such as aluminum methoxide, aluminum ethoxide, aluminum propoxide, aluminum butoxide, aluminum amyloxide, aluminum hexyloxide, aluminum cyclopentoxide, aluminum cyclohexyloxide, aluminum allyloxide, aluminum phenoxide, aluminum methoxyethoxide, aluminum ethoxyethoxide, aluminum dipropoxyethylacetoacetate, aluminum dibutoxyethylacetoacetate, aluminum propoxybisethylacetoacetate, aluminum butoxybisethylacetoacetate, aluminum 2,4-pentanedionate, aluminum 2,2,6,6-tetramethyl-3,5-heptanedionate, and the like.

In case that U is gallium, examples of the compound represented by the general formula (2) include monomers such as gallium methoxide, gallium ethoxide, gallium propoxide, gallium butoxide, gallium amyloxide, gallium hexyloxide, gallium cyclopentoxide, gallium cyclohexyloxide, gallium allyloxide, gallium phenoxide, gallium methoxyethoxide, gallium ethoxyethoxide, gallium dipropoxyethylacetoacetate, gallium dibutoxyethylacetoacetate, gallium propoxybisethylacetoacetate, gallium butoxybisethylacetoacetate, gallium 2,4-pentanedionate, gallium 2,2,6,6-tetramethyl-3,5-heptanedionate, and the like.

In case that U is yttrium, examples of the compound represented by the general formula (2) include monomers such as yttrium methoxide, yttrium ethoxide, yttrium propoxide, yttrium butoxide, yttrium amyloxide, yttrium hexyloxide, yttrium cyclopentoxide, yttrium cyclohexyloxide, yttrium allyloxide, yttrium phenoxide, yttrium methoxyethoxide, yttrium ethoxyethoxide, yttrium dipropoxyethylacetoacetate, yttrium dibutoxyethylacetoacetate, yttrium propoxybisethylacetoacetate, yttrium butoxybisethylacetoacetate, yttrium 2,4-pentanedionate, yttrium 2,2,6,6-tetramethyl-3,5-heptanedionate, and the like.

In case that U is germanium, examples of the compound represented by the general formula (2) include monomers such as germanium methoxide, germanium ethoxide, germanium propoxide, germanium butoxide, germanium amyloxide, germanium hexyloxide, germanium cyclopentoxide, germanium cyclohexyloxide, germanium allyloxide, germanium phenoxide, germanium methoxyethoxide, germanium ethoxyethoxide, and the like.

In case that U is titanium, examples of the compound represented by the general formula (2) include monomers such as titanium methoxide, titanium ethoxide, titanium propoxide, titanium butoxide, titanium amyloxide, titanium hexyloxide, titanium cyclopentoxide, titanium cyclohexyloxide, titanium allyloxide, titanium phenoxide, titanium methoxyethoxide, titanium ethoxyethoxide, titanium dipropoxyethylacetoacetate, titanium dibutoxybisethylacetoacetate, titanium dipropoxy bis(2,4-pentanedionate), titanium dibutoxy bis(2,4-pentanedionate), and the like.

In case that U is hafnium, examples of the compound represented by the general formula (2) include monomers such as hafnium methoxide, hafnium ethoxide, hafnium propoxide, hafnium butoxide, hafnium amyloxide, hafnium hexyloxide, hafnium cyclopentoxide, hafnium cyclohexyloxide, hafnium allyloxide, hafnium phenoxide, hafnium methoxyethoxide, hafnium ethoxyethoxide, hafnium dipropoxybisethylacetoacetate, hafnium dibutoxybisethylacetoacetate, hafnium dipropoxy bis(2,4-pentanedionate), hafnium dibutoxy bis(2,4-pentanedionate), and the like In case that U is tin, examples of the compound represented by the general formula (2) include monomers such as tin methoxide, tin ethoxide, tin propoxide, tin butoxide, tin phenoxide, tin methoxyethoxide, tin ethoxyethoxide, tin 2,4-pentanedionate, tin 2,2,6,6-tetramethyl-3,5-heptanedionate, and the like.

In case that U is arsenic, examples of the compound represented by the general formula (2) include monomers such as arsenic methoxide, arsenic ethoxide, arsenic propoxide, arsenic butoxide, arsenic phenoxide, and the like.

In case that U is antimony, examples of the compound represented by the general formula (2) include monomers such as antimony methoxide, antimony ethoxide, antimony propoxide, antimony butoxide, antimony phenoxide, antimony acetate, antimony propionate, and the like.

In case that U is niobium, examples of the compound represented by the general formula (2) include monomers such as niobium methoxide, niobium ethoxide, niobium propoxide, niobium butoxide, niobium phenoxide, and the like.

In case that U is tantalum, examples of the compound represented by the general formula (2) include monomers such as tantalum methoxide, tantalum ethoxide, tantalum propoxide, tantalum butoxide, tantalum phenoxide, and the like.

In case that U is bismuth, examples of the compound represented by the general formula (2) include monomers such as bismuth methoxide, bismuth ethoxide, bismuth propoxide, bismuth butoxide, bismuth phenoxide, and the like.

In case that U is phosphorus, examples of the compound represented by the general formula (2) include monomers such as trimethyl phosphate, triethyl phosphate, tripropyl phosphate, trimethyl phosphite, triethyl phosphite, tripropyl phosphite, diphosphorus pentoxide and the like.

In case that U is vanadium, examples of the compound represented by the general formula (2) include monomers such as vanadium oxide bis(2,4-pentanedionate), vanadium 2,4-pentanedionate, vanadium tributoxide oxide, vanadium tripropoxide oxide, and the like.

In case that U is zirconium, examples of the compound represented by the general formula (2) include monomers such as zirconium methoxide, zirconium ethoxide, zirconium propoxide, zirconium butoxide, zirconium phenoxide, zirconium dibutoxide bis(2,4-pentanedionate), zirconium dipropoxide bis(2,2,6,6-tetramethyl-3,5-heptanedionate), and the like.

More preferable as the polysiloxane compound are those each containing therein a component derived from a tetrafunctional hydrolyzable monomer, in an amount of 70 mole % or more of the polysiloxane.

[Other Components]

(Thermal Cross-Linking Accelerator)

In the present invention, it is possible to blend a thermal cross-linking accelerator into the silicon-containing resist lower layer film-forming composition. Examples of blendable thermal cross-linking accelerators include compounds each represented by the following general formula (3) or (4). Specifically, it is possible to add the material described in the Patent Document 6.

$$L_aH_bX \quad (3)$$

(in the formula,

L is lithium, sodium, potassium, rubidium, or cesium;

X is a hydroxyl group, or a monovalent, divalent, or higher organic acid group having 1 to 30 carbon atoms;

a is an integer of 1 or greater;

b is an integer of 0, 1, or greater; and a+b is a valence of the hydroxyl group or organic acid group),

$$MY \quad (4)$$

wherein

M represents sulfonium, iodonium, or ammonium; and

Y represents a nonnucleophilic counter ion.

It is noted that the thermal cross-linking accelerators may be used solely in one kind, or mixedly in two or more kinds. The addition amount of the thermal cross-linking accelerator is preferably between 0.01 and 50 parts by mass, more preferably between 0.1 and 40 parts by mass, relative to 100 parts by mass of the polysiloxane as the base polymer.

(Organic Acid)

To improve the stability of the silicon-containing resist lower layer film-forming composition of the present invention, it is preferable to add thereinto a monovalent, divalent, or higher organic acid having 1 to 30 carbon atoms. Examples of the acid to be added at this time include formic acid, acetic acid, propionic acid, butanoic acid, pentanoic acid, hexanoic acid, heptanoic acid, octanoic acid, nonanoic acid, decanoic acid, oleic acid, stearic acid, linolic acid, linoleic acid, benzoic acid, phthalic acid, isophthalic acid, terephthalic acid, salicylic acid, trifluoroacetic acid, monochloroacetic acid, dichloroacetic acid, trichloroacetic acid, oxalic acid, malonic acid, methylmalonic acid, ethylmalonic acid, propylmalonic acid, butylmalonic acid, dimethylmalonic acid, diethylmalonic acid, succinic acid, methylsuccinic acid, glutaric acid, adipic acid, itaconic acid, maleic acid, fumaric acid, citraconic acid, citric acid, and the like. Preferable among them are oxalic acid, maleic acid, formic acid, acetic acid, propionic acid, citric acid, and the like. To keep the stability, it is possible to use two or more kinds of these acids in a mixed manner. The addition amount thereof is to be between 0.001 and 25 parts by mass, preferably between 0.01 and 15 parts by mass, and more preferably between 0.1 and 5 parts by mass, relative to 100 parts by mass of silicon to be contained in the composition.

Alternatively, it is preferable to blend the organic acid(s) into the composition in terms of its pH, to preferably attain $0 \leq pH \leq 7$, more preferably $0.3 \leq pH \leq 6.5$, and most preferably $0.5 \leq pH \leq 6$.

(Water)

In the present invention, it is possible to add water into the composition. Addition of water causes hydration of the polysiloxane compound in the composition, thereby improving the lithography performance. The content ratio of water in the solvent components of the composition is to be between 0 mass % exclusive and 50 mass % exclusive, more preferably between 0.3 and 30 mass %, and most preferably between 0.5 and 20 mass %. Excessively larger addition amounts of respective components lead to deteriorated uniformities of silicon-containing resist lower layer films, thereby possibly causing eye hole at the worst. In turn, excessively smaller addition amounts possibly cause deteriorated lithography performances.

The usage amount of all the solvents inclusive of water is to be between 100 and 100,000 parts by mass, and preferably between 200 and 50,000 parts by mass, relative to 100 parts by mass of the polysiloxane compound as the base polymer.

(Photoacid Generator)

In the present invention, it is possible to add a photoacid generator into the composition. As the photoacid generator to be used in the present invention, it is specifically possible to add a material described in paragraphs (0160) to (0179) of JP2009-126940A.

(Stabilizer)

Further, in the present invention, it is possible to add a stabilizer into the composition. As the stabilizer, it is possible to add a monohydric, dihydric, or higher alcohol having a cyclic ether as a substitutional group. Particularly, it is possible to improve the stability of the silicon-containing resist lower layer film-forming composition by adding a stabilizer described in paragraphs (0181) and (0182) of JP2009-126940A.

(Surfactant)

Furthermore, in the present invention, it is possible to add a surfactant into the composition. As such a substance, it is specifically possible to add a material described in a paragraph (0185) of JP2009-126940A.

(Other Components)

Moreover, it is possible in the present invention to add a high-boiling solvent having a boiling point of 180 degrees or higher into the composition as required. Examples of such a high-boiling solvent include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, ethylene glycol monoethyl ether acetate, 1,2-diacetoxyethane, 1-acetoxy-2-methoxyethane, 1,2-diacetoxypropane, diethylene glycol monomethyl ether acetate, diethylene glycol monoethyl ether acetate, diethylene glycol mono-n-butyl ether acetate, propylene glycol monomethyl ether acetate, propylene glycol monopropyl ether acetate, propylene glycol monobutyl ether acetate, dipropylene glycol monomethyl ether acetate, dipropylene glycol monoethyl ether acetate, and the like.

Containing the high-boiling solvent having a boiling point of 180 degrees or higher enables to form a resist lower layer film which is excellent in adherence with an upper layer resist pattern.

[Negative Patterning Process]

(Negative Patterning Process 1)

The present invention provides a patterning process (so-called "multi-layer resist method") comprising the steps of using a coating type of organic lower layer film material, to form a lower organic layer film on a substance to be processed;

using the above-described silicon-containing resist lower layer film-forming composition, to form a silicon-containing resist lower layer film on the lower organic layer film;

using a chemically amplified resist composition, to form a photoresist film on the silicon-containing resist lower layer film;

heat-treating the photoresist film, then exposing the photoresist film to a high energy beam, and subsequently using an organic solvent-based developer to dissolve a non-exposed portion of the photoresist film, thereby forming a negative pattern through the photoresist film;

transferring the negative pattern formed through the photoresist film onto the silicon-containing resist lower layer film by dry etching, by using the photoresist film as a mask;

transferring the thus obtained resist lower layer film pattern onto the lower organic layer film by dry etching, by using the resist lower layer film as a mask; and transferring the thus obtained lower organic layer film pattern onto the substance to be processed, by dry etching, by using the lower organic layer film as a mask.

(Negative Patterning Process 2)

Further, the present invention provides a patterning process comprising the steps of:

forming an organic hard mask containing carbon as a main component, on a substance to be processed, by a CVD technique;

using the above-described silicon-containing resist lower layer film-forming composition, to form a silicon-containing resist lower layer film on the organic hard mask;

using a chemically amplified resist composition, to form a photoresist film on the silicon-containing resist lower layer film;

heat-treating the photoresist film, then exposing the photoresist film to a high energy beam, and subsequently using an organic solvent-based developer to dissolve a non-exposed portion of the photoresist film, thereby forming a negative pattern through the photoresist film;

transferring the negative pattern formed through the photoresist film onto the silicon-containing resist lower layer film by dry etching, by using the photoresist film as a mask;

transferring the thus obtained resist lower layer film pattern onto the organic hard mask by dry etching, by using the resist lower layer film as a mask; and transferring the thus obtained organic hard mask pattern onto the substance to be processed, by dry etching, by using the organic hard mask as a mask.

When the negative pattern is formed while using the resist lower layer film-forming composition of the present invention, it is possible to form the pattern formed of the photoresist onto a substrate without causing a size conversion difference, by optimizing the combination with the CVD film or lower organic layer film as described above.

Further, it is preferable that the difference between the contact angle of the silicon-containing resist lower layer film and the contact angle of the upper layer resist (resist pattern) after negative development, is 10 degrees or less.

Smaller differences of 10 degrees or less between the contact angle of the silicon-containing resist lower layer film and the contact angle of the upper layer resist after negative development, improve adhesion therebetween to prevent pattern collapse, thereby enabling to form fine patterns.

The silicon-containing resist lower layer film to be used in the patterning process of the present invention can be fabricated from the silicon-containing resist lower layer film-forming composition of the present invention on a substance to be processed by a spin coating method or the like in the same manner as a photoresist film. After spin coating, it is desirable to evaporate the solvent of the composition, and to bake the latter so as to promote a cross-linking reaction, for prevention of mixing thereof with a photoresist film. Preferably used therefor are a baking temperature within a range of 50 to 500° C., and a baking time within a range of 10 to 300 seconds. Although depending on a structure of a device to be produced, the particularly preferable temperature range is 400° C. or lower so as to reduce a thermal damage to the device.

Here, it is possible to adopt, as the substance to be processed, a semiconductor device substrate itself, or a semiconductor device substrate formed thereon with any one of a metal film, an alloy film, a metal carbide film, a metal oxide film, a metal nitride film, a metal oxide carbide film, and a metal oxide nitride film, as a layer to be processed (portion to be processed).

Typically used as the semiconductor device substrate is a silicon substrate, without particularly limited thereto, and it is also possible to use a substrate which is different from the layer to be processed in material and which is made of Si, amorphous silicon (α-Si), p-Si, $SiO_2$, SiN, SiON, W, TiN, Al, or the like.

Usable as a metal constituting the substance to be processed, is any one of silicon, gallium, titanium, tungsten, hafnium, zirconium, chromium, germanium, copper, aluminum, and iron, or an alloy of one or more of these metals. Exemplarily used as a layer to be processed containing such a metal, are Si, $SiO_2$, SiN, SiON, SiOC, p-Si, α-Si, TiN, WSi, BPSG, SOG, Cr, CrO, CrON, MoSi, W, W—Si, Al, Cu, Al—Si, or the like, various low dielectric films, an etching stopper film therefor, and the like, which can each be typically formed into a thickness between 50 and 10,000 nm, particularly between 100 and 5,000 nm.

In the negative patterning process of the present invention, the photoresist film is of a chemically amplified type, without particularly limitation, insofar as the same is capable of forming a negative pattern by development using a developer comprising an organic solvent.

For example, when the exposure step in the present invention is conducted as an exposure process by an ArF excimer laser light, it is possible to use any one of typical resist compositions for an ArF excimer laser light, as the photoresist film.

As such a resist composition for an ArF excimer laser light, many resins have been already known as candidates, and such already known resins are generally classified into poly(meth)acrylic-based ones, COMA (Cyclo Olefin Maleic Anhydride) based ones, COMA-(meth)acrylic hybrid-based ones, ROMP (ring-opening metathesis polymerization) based ones, polynorbornene-based ones, and the like. Among them, resist compositions adopting the poly(meth)acrylic-based resins each having an alicyclic structure in the side-chain to thereby ensure an etching resistance, are excellent in resolution performance as compared to those compositions based on the other resins.

After forming the silicon-containing resist lower layer film in the negative patterning process, the photoresist film is formed thereon by using the photoresist composition solution, in a manner to preferably adopt the spin coating method similarly to the silicon-containing resist lower layer film. After spin coating of the photoresist composition, prebaking is to be conducted, preferably at a temperature within a range of 80 and 180° C., and for a time within a range of 10 and 300 seconds. Thereafter, exposure is conducted, followed by conduction of organic solvent development, thereby obtaining a negative resist pattern. After exposure, post-exposure bake (PEB) is to be preferably conducted.

Exemplarily usable as an organic solvent-based developer is one containing, as its component(s), one or more kinds selected from among 2-octanone, 2-nonanone, 2-heptanone, 3-heptanone, 4-heptanone, 2-hexanone, 3-hexanone, diisobutylketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate; where it is preferable to use such a developer that the total amount of one kind or two or more kinds of the components of the developer is 50 mass % or more, from a standpoint of prevention of pattern collapse.

In case of etching the silicon-containing resist lower layer film in the patterning process of the present invention, the etching is to be conducted by using a gas containing fluorine as a main component, such as a fluorocarbon-based gas or the like. For smaller amounts of photoresist film loss, the silicon-containing resist lower layer film is to preferably exhibit a faster etching rate to such a gas.

In case of providing the lower organic layer film between the silicon-containing resist lower layer film and the substance to be processed in such a multi-layer resist method in a manner to use the lower organic layer film as an etching mask for the substance to be processed, the lower organic layer film is to be preferably an organic film having an aromatic structure. However, when the lower organic layer film is a sacrificial film, the former may be a silicon-containing lower organic layer film insofar as its silicon content is 15 mass % or less.

Usable as such a lower organic layer film are: those already known as lower layer films for a three-layer resist method, or a two-layer resist method using a silicon resist composition; a 4,4'-(9-fluorenylidene)bisphenol novolac resin (molecular weight 11,000) described in JP2005-128509; numerous resins represented by a novolak resin, such as those resins each known as a resist lower layer film material for a two-layer resist method or a three-layer resist method; and the like. Further, in case of intending to enhance a heat resistance than a typical novolak, it is possible to incorporate a polycyclic structure such as a 6,6'-(9-fluorenylidene)-di(2-naphthol) novolac resin, or to select a polyimide-based resin (JP2004-153125, for example).

The lower organic layer film can be formed on the substance to be processed by using a composition solution by spin coating or the like, similarly to the photoresist composition. After forming the lower organic layer film by spin coating or the like, the film is to be desirably baked to evaporate the organic solvent therein. Preferably used therefor are a baking temperature within a range of 80 to 300° C., and a baking time within a range of 10 to 300 seconds.

Although depending on an etching process condition, it is preferable that a lower organic layer film has a thickness of 5 nm or thicker, particularly 20 nm or thicker, and 50,000 nm or thinner without particularly limited thereto, and the silicon-containing resist lower layer film according to the present invention is to preferably have a thickness between 1 nm inclusive and 500 nm inclusive, more preferably 300 nm or thinner, and most preferably 200 nm or thinner. Further, the photoresist film is to preferably have a thickness between 1 nm inclusive and 200 nm inclusive.

[Patterning Process of the Present Invention by Three-Layer Resist Method]

The negative patterning process of the present invention by the three-layer resist method as described above is as follows (see FIG. 1). Firstly fabricated in this process is a lower organic layer film 2 on a substance to be processed 1, by spin coating (FIG. 1(I-A)). Since this lower organic layer film 2 is to act as a mask upon etching the substance to be processed 1, the film 2 is to be desirably high in etching resistance. Further, since the film 2 is required not to be mixed with the silicon-containing resist lower layer film as an upper layer, the film 2 is to be desirably crosslinked by heat or acid after formation thereof by spin coating.

To be formed on the organic layer film is a silicon-containing resist lower layer film 3 by a spin coating method by using the silicon-containing resist lower layer film-forming composition of the present invention (FIG. 1(I-B)), followed by formation thereon of a photoresist film 4 by a spin coating method (FIG. 1(I-C)). It is noted that the silicon-containing resist lower layer film 3 can be formed by such a composition that, when the photoresist film 4 is exposed, that portion of the silicon-containing resist lower layer film 3 corresponding to the exposed portion of the photoresist film has a contact angle between 40 degree inclusive and 70 degree exclusive relative to pure water, after exposure.

The photoresist film 4 is subjected to pattern formation in the usual manner by using a mask 5, by means of patterning exposure using a light source P suitable for the photoresist film 4, such as KrF excimer laser light, ArF excimer laser light, $F_2$ laser light, or EUV light, and preferably using either photolithography at a wavelength between 10 nm inclusive and 300 nm inclusive, direct drawing by an electron beam, or nano-imprinting, or combination thereof (FIG. 1(I-D)); then a heat treatment is conducted under a condition matching the applicable photoresist film (FIG. 1(I-E)); followed by development operation by an organic developer (negative development), and followed by conduction of rinsing as required, thereby enabling to obtain a negative resist pattern 4a (FIG. 1(I-F)).

Next, etching for the silicon-containing resist lower layer film 3 is conducted by using the negative resist pattern 4a as an etching mask, under such a dry etching condition exhibiting a predominantly higher etching rate for the film 3, such as by a fluorine-based gas plasma. As a result, it is possible to obtain a negative pattern 3a of silicon-containing resist lower layer film, substantially without influence of pattern change of the resist film due to side etching (FIG. 1(I-G)).

Then, for the substrate having thereon the negative pattern 3a of silicon-containing resist lower layer film to which the above obtained negative resist pattern 4a has been transferred, reactive dry etching is conducted under such a dry etching condition exhibiting a predominantly higher etching rate for the lower organic layer film 2, such as by reactive dry etching based on gas plasma containing oxygen, or by reactive dry etching based on gas plasma containing hydrogen-nitrogen, thereby etching the lower organic layer film 2. While this etching step brings about obtainment of a negative pattern 2a of lower organic layer film, the photoresist film at the uppermost layer is typically lost simultaneously therewith (FIG. 1(I-H)). Further, the negative pattern 2a of lower organic layer film obtained here is used as an etching mask to conduct dry etching of the substance to be processed 1, such as fluorine-based dry etching or chlorine-based dry etching, thereby enabling to etch the substance to be processed 1 with a higher precision and to transfer the negative pattern 2a to the sub as a negative pattern 1a (FIG. 1(I-I)).

In the processes of the three-layer resist method, it is also possible to use an organic hard mask formed by a CVD method, instead of the lower organic layer film 2. Also in such a case, it is possible to conduct the processing of the substance to be processed 1 in the same procedures as the above.

EXAMPLE

Although the present invention will be explained hereinafter in more detail by describing Synthesis Examples, Examples, and Comparative Examples, the present invention is not limited to the descriptions thereof. In the following Examples, "%" means a mass %, and measurement of molecular weight was conducted by GPC.

Synthesis of Surface Modifier Component

Synthesis Example 1-1

Added into a mixture of 200 g of methanol, 0.1 g of methanesulfonic acid, and 60 g of deionized water, was another mixture of 47.7 g of Monomer 101 and 43.0 g of Monomer 102, and the resultant mixture was kept at 40° C. for 12 hours to carry out hydrolytic condensation. Added thereinto after completion of the reaction, was 200 g of propylene glycol ethyl ether (PGEE), thereby distillingly removing by-product alcohols under reduced pressure. Added thereinto were 1,000 ml of ethyl acetate and 100 g of PGEE, thereby separating a water layer therefrom. Added into the residual organic layer was 100 ml of ion exchange water, followed by stirring, still standing, and liquid separation. This was repeated three times. The residual organic layer was concentrated under reduced pressure, thereby obtaining 200 g of PGEE solution (compound concentration of 20%) of silicon-containing compound 1-1. Its molecular weight relative to polystyrene standards was measured to be Mw=2,100. Further, it was revealed from $^1$H-NMR that all ethoxyethyl groups as protective groups were removed.

Applicable Monomers listed in Table 1 were used under the same condition as Synthesis Example 1-1, thereby conducting [Synthesis Example 1-4], and [Synthesis Example 1-8] to [Synthesis Example 1-13] to obtain intended substances, respectively.

Synthesis Example 1-2

Added into a mixture of 400 g of ethanol, 60 g of 25% tetramethylammonium hydroxide, and 140 g of deionized water, was another mixture of 47.7 g of Monomer 101 and 42.7 g of Monomer 121, and the resultant mixture was kept at 40° C. for 4 hours to carry out hydrolytic condensation. Added thereinto after completion of the reaction, was 20 g of acetic acid for neutralization, thereby distillingly removing by-product alcohols under reduced pressure. Added thereinto were 1,200 ml of ethyl acetate and 350 g of PGEE, thereby separating a water layer therefrom. Added into the residual organic layer was 100 ml of ion exchange water, followed by stirring, still standing, and liquid separation. This was repeated three times. The residual organic layer was concentrated under reduced pressure, thereby obtaining 280 g of PGEE solution (compound concentration of 20%) of silicon-containing compound 1-2. Its molecular weight relative to polystyrene standards was measured to be Mw=2,600. Further, it was revealed from $^1$H-NMR that all acetyl groups as protective groups were removed.

Applicable Monomers listed in Table 1 were used under the same condition as [Synthesis Example 1-2], thereby conducting [Synthesis Example 1-3], [Synthesis Example 1-5], [Synthesis Example 1-6], and [Synthesis Example 1-7] to obtain intended substances, respectively.

TABLE 1

| Synthesis Example | Reaction starting material | Mw |
|---|---|---|
| 1-1 | Monomer 101: 47.7 g, Monomer 120: 43 g | 2100 |
| 1-2 | Monomer 101: 47.7 g, Monomer 121: 42.7 g | 2600 |
| 1-3 | Monomer 101: 47.7 g, Monomer 122: 42.7 g | 2900 |
| 1-4 | Monomer 101: 47.7 g, Monomer 123: 39.7 g | 1600 |
| 1-5 | Monomer 101: 47.7 g, Monomer 124: 45.7 g | 3000 |
| 1-6 | Monomer 101: 40.9 g, Monomer 102: 7.6 g, Monomer 125: 35.5 g | 2500 |
| 1-7 | Monomer 101: 40.9 g, Monomer 102: 7.6 g, Monomer 126: 43.6 g | 3100 |
| 1-8 | Monomer 101: 54.5 g, Monomer 127: 13.5 g, Monomer 120: 14.3 g | 1500 |
| 1-9 | Monomer 101: 61.3 g, Monomer 128: 14.1 g | 1600 |
| 1-10 | Monomer 101: 47.7 g, Monomer 120: 14.3 g, Monomer 127: 13.5 g | 1900 |
| 1-11 | Monomer 101: 47.7 g, Monomer 120: 14.3 g, Monomer 128: 14.1 g | 2200 |
| 1-12 | Monomer 101: 47.7 g, Monomer 120: 14.3 g, Monomer 127: 13.5 g, Monomer 128: 14.1 g | 2300 |
| 1-13 | Monomer 100: 19.8 g, Monomer 101: 27.2 g, Monomer 102: 30.4 g | 1700 |

TABLE 2

| Structure | Name |
|---|---|
| PhSi(OCH$_3$)$_3$ | Monomer 100 |
| CH$_3$Si(OCH$_3$)$_3$ | Monomer 101 |
| Si(OCH$_3$)$_4$ | Monomer 102 |
| (CH$_3$O)$_3$Si—C$_6$H$_4$—CH$_3$ | Monomer 104 |
| (CH$_3$O)$_3$Si—C$_6$H$_4$—OCH$_3$ | Monomer 105 |
| B(OC$_3$H$_7$)$_3$ | Monomer 110 |
| Ti(OC$_4$H$_9$)$_4$ | Monomer 111 |
| Ge(OC$_4$H$_9$)$_4$ | Monomer 112 |
| P$_2$O$_5$ | Monomer 113 |
| Al[CH$_3$COCH=C(O—)CH$_3$]$_3$ | Monomer 114 |
| (CH$_3$O)$_3$Si—C$_6$H$_4$—O—CH(CH$_3$)—O—C$_2$H$_5$ | Monomer 120 |
| (CH$_3$O)$_3$Si—CH$_2$CH$_2$—C$_6$H$_4$—O—C(O)CH$_3$ | Monomer 121 |
| (CH$_3$O)$_3$Si—CH$_2$CH$_2$—C$_6$H$_4$—C(O)OMe | Monomer 122 |
| (CH$_3$O)$_3$Si—(CH$_2$)$_3$—O-THP | Monomer 123 |
| (CH$_3$O)$_3$Si-norbornyl-CH$_2$—O—C(O)CH$_3$ | Monomer 124 |
| (CH$_3$O)$_3$Si—(CH$_2$)$_4$—C(O)OMe | Monomer 125 |
| (CH$_3$O)$_3$Si-norbornyl-C(O)OMe (OMe substituent) | Monomer 126 |
| (CH$_3$O)$_3$Si—C$_6$H$_4$—O—CH(CH$_3$)—O—C$_2$H$_5$ | Monomer 127 |
| (CH$_3$)$_2$(CH$_3$O)Si—CH$_2$CH$_2$—C$_6$H$_4$—O—CH(CH$_3$)—O—C$_2$H$_5$ | Monomer 128 |

Synthesis of Polymer Component

Synthesis Example 2-1

Added into a mixture of 120 g of methanol, 0.1 g of 70% nitric acid, and 60 g of deionized water, was another mixture of 5.0 g of Monomer 100, 3.4 g of Monomer 101, and 68.5 g of Monomer 102, and the resultant mixture was kept at 40° C. for 12 hours to carry out hydrolytic condensation. Added thereinto after completion of the reaction, was 300 g of PGEE, thereby distillingly removing by-product alcohols and excessive water under reduced pressure, to obtain 320 g of PGEE solution (polymer concentration of 10%) of polysiloxane compound 2-1. Its molecular weight relative to polystyrene standards was measured to be Mw=2,300.

Applicable Monomers listed in Table 2 were used under the same condition as Synthesis Example 2-1, thereby conducting [Synthesis Example 2-2] to [Synthesis Example 2-8] to obtain intended substances, respectively.

TABLE 3

| Synthesis Example | Reaction starting material | Mw |
|---|---|---|
| 2-1 | Monomer 100: 5.0 g, Monomer 101: 3.4 g, Monomer 102: 68.5 g | 2300 |
| 2-2 | Monomer 100: 5.0 g, Monomer 101: 3.4 g, Monomer 102: 60.9 g, Monomer 110: 9.4 g | 3800 |

TABLE 3-continued

| Synthesis Example | Reaction starting material | Mw |
|---|---|---|
| 2-3 | Monomer 100: 5.0 g, Monomer 101: 3.4 g, Monomer 102: 60.9 g, Monomer 111: 17.0 g | 3900 |
| 2-4 | Monomer 100: 5.0 g, Monomer 101: 3.4 g, Monomer 102: 60.9 g, Monomer 112: 18.3 g | 3900 |
| 2-5 | Monomer 100: 5.0 g, Monomer 101: 3.4 g, Monomer 102: 60.9 g, Monomer 113: 14.2 g | 3900 |
| 2-6 | Monomer 104: 5.3 g, Monomer 101: 3.4 g, Monomer 102: 60.9 g, Monomer 114: 16.2 g | 3600 |
| 2-7 | Monomer 105: 5.7 g, Monomer 101: 17.0 g, Monomer 102: 53.3 g | 3200 |
| 2-8 | Monomer 100: 5.0 g, Monomer 101: 23.8 g, Monomer 102: 45.7 g | 2200 |

Examples and Comparative Examples

Mixed at ratios listed in Table 4-1 and Table 4-2 were silicon-containing surface modifiers (1-1) to (1-13) obtained in the above Synthesis Examples, polysiloxane compounds (2-1) to (2-8) as polymer components, acids, thermal cross-linking accelerators, solvents, and additives, respectively, followed by filtration by a filter made of 0.1 μm fluororesin, thereby preparing silicon-containing film-forming composition solutions, which were labelled as Sol. 1 to Sol. 30, respectively.

TABLE 4-1

| | Silicon-containing surface modifier (parts by mass) | Poly-siloxane (parts by mass) | Thermal cross-linking accelerator (parts by mass) | Photoacid generator (parts by mass) | Acid (parts by mass) | Solvent (parts by mass) | Water (parts by mass) |
|---|---|---|---|---|---|---|---|
| Sol. 1 | 1-1 (0.1) | 2-1 (3.9) | TPSOH (0.04) | None | Maleic acid (0.04) | PGEE (150) | Water (15) |
| Sol. 2 | 1-1 (0.1) | 2-1 (3.9) | TPSHCO$_3$ (0.04) | None | Oxalic acid (0.04) | PGEE (150) | Water (15) |
| Sol. 3 | 1-1 (0.1) | 2-1 (3.9) | TPSOx (0.04) | None | Maleic acid (0.04) | PGEE (150) | Water (15) |
| Sol. 4 | 1-1 (0.1) | 2-1 (3.9) | TPSTFA (0.04) | None | Maleic acid (0.04) | PGEE (150) | Water (15) |
| Sol. 5 | 1-1 (0.1) | 2-1 (3.9) | TPSOCOPh (0.04) | None | Oxalic acid (0.04) | PGEE (150) | Water (15) |
| Sol. 6 | 1-1 (0.1) | 2-1 (3.9) | TPSH$_2$PO$_4$ (0.04) | None | Oxalic acid (0.04) | PGEE (150) | Water (15) |
| Sol. 7 | 1-1 (0.1) | 2-1 (3.9) | QMAMA (0.04) | None | Maleic acid (0.04) | PGEE (150) | Water (15) |
| Sol. 8 | 1-1 (0.1) | 2-1 (3.9) | QBANO$_3$ (0.04) | None | Maleic acid (0.04) | PGEE (150) | Water (15) |
| Sol. 9 | 1-1 (0.1) | 2-1 (3.9) | QMATFA (0.04) | TPSNf (0.04) | Maleic acid (0.04) | PGEE (150) | Water (15) |
| Sol. 10 | 1-1 (0.1) | 2-1 (3.9) | Ph$_2$ICl (0.04) | None | Maleic acid (0.04) | PGEE (135) GBL (15) | Water (15) |
| Sol. 11 | 1-1 (0.1) | 2-1 (3.9) | TPSMA (0.04) | None | Maleic acid (0.04) | PGEE (150) | Water (15) |
| Sol. 12 | 1-2 (0.1) | 2-1 (3.9) | TPSMA (0.04) | None | Maleic acid (0.04) | PGEE (150) | Water (15) |
| Sol. 13 | 1-3 (0.1) | 2-1 (3.9) | TPSMA (0.04) | None | Maleic acid (0.04) | PGEE (150) | Water (15) |
| Sol. 14 | 1-4 (0.1) | 2-1 (3.9) | TPSMA (0.04) | None | Maleic acid (0.04) | PGEE (150) | Water (15) |
| Sol. 15 | 1-5 (0.1) | 2-1 (3.9) | TPSMA (0.04) | None | Maleic acid (0.04) | PGEE (150) | Water (15) |

TABLE 4-2

| | Silicon-containing surface modifier (parts by mass) | Poly-siloxane (parts by mass) | Thermal cross-linking accelerator (parts by mass) | Photoacid generator (parts by mass) | Acid (parts by mass) | Solvent (parts by mass) | Water (parts by mass) |
|---|---|---|---|---|---|---|---|
| Sol. 16 | 1-6 (0.1) | 2-1 (3.9) | TPSMA (0.04) | None | Oxalic acid (0.04) | PGEE (150) | Water (15) |
| Sol. 17 | 1-7 (0.1) | 2-1 (3.9) | TPSMA (0.04) | None | Maleic acid (0.04) | PGEE (150) | Water (15) |
| Sol. 18 | 1-8 (0.1) | 2-1 (3.9) | TPSMA (0.04) | None | Maleic acid (0.04) | PGEE (150) | Water (15) |

TABLE 4-2-continued

| | Silicon-containing surface modifier (parts by mass) | Polysiloxane (parts by mass) | Thermal cross-linking accelerator (parts by mass) | Photoacid generator (parts by mass) | Acid (parts by mass) | Solvent (parts by mass) | Water (parts by mass) |
|---|---|---|---|---|---|---|---|
| Sol. 19 | 1-9 (0.1) | 2-1 (3.9) | TPSMA (0.04) | None | Maleic acid (0.04) | PGEE (150) | Water (15) |
| Sol. 20 | 1-10 (0.1) | 2-1 (3.9) | TPSMA (0.04) | TPSNf (0.04) | Maleic acid (0.04) | PGEE (150) | Water (15) |
| Sol. 21 | 1-11 (0.1) | 2-1 (3.9) | TPSMA (0.04) | None | Maleic acid (0.04) | PGEE (150) | Water (15) |
| Sol. 22 | 1-12 (0.1) | 2-1 (3.9) | TPSMA (0.04) | None | Maleic acid (0.04) | PGEE (150) | Water (15) |
| Sol. 23 | 1-1 (0.1) | 2-2 (3.9) | TPSMA (0.04) | None | Maleic acid (0.04) | PGEE (135) GBL (15) | Water (15) |
| Sol. 24 | 1-1 (0.1) | 2-3 (3.9) | TPSMA (0.04) | None | Maleic acid (0.04) | PGEE (150) | Water (15) |
| Sol. 25 | 1-1 (0.1) | 2-4 (3.9) | TPSMA (0.04) | None | Maleic acid (0.04) | PGEE (135) GBL (15) | Water (15) |
| Sol. 26 | 1-1 (0.1) | 2-5 (3.9) | TPSMA (0.04) | None | Maleic acid (0.04) | PGEE (150) | Water (15) |
| Sol. 27 | 1-1 (0.1) | 2-6 (3.9) | TPSMA (0.04) | None | Maleic acid (0.04) | PGEE (150) | Water (15) |
| Sol. 28 | 1-1 (0.1) | 2-7 (3.9) | TPSMA (0.04) | None | Maleic acid (0.04) | PGEE (150) | Water (15) |
| Sol. 29 | 1-1 (0.1) | 2-8 (3.9) | TPSMA (0.04) | None | Maleic acid (0.04) | PGEE (150) | Water (15) |
| Sol. 30 | 1-13 (0.1) | 2-1 (3.9) | TPSMA (0.04) | None | Maleic acid (0.04) | PGEE (150) | Water (15) |

TPSOH: triphenylsulfonium hydroxide
TPSHCO$_3$: mono(triphenylsulfonium)carbonate
TPSO$_x$: mono(triphenylsulfonium)oxalate
TPSTFA: triphenylsulfonium trifluoroacetate
TPSOCOPh: triphenylsulfonium benzoate
TPSH$_2$PO$_4$: mono(triphenylsulfonium)phosphate
TPSMA: mono(triphenylsulfonium)maleate
TPSNf: triphenylsulfonium nonafluorobutanesulfonate
QMAMA: mono(tetramethylammonium)maleate
QMATFA: tetramethylammonium trifluoroacetate
QBANO$_3$: tetrabutylammonium nitrate
Ph$_2$ICl: diphenyliodonium chloride
PGEE: propylene glycol ethyl ether
GBL: gamma-butyrolactone
Measurement of Contact Angle
<Contact Angle Sample of Lower Layer Film Only>

Silicon-containing resist lower layer film-forming compositions Sol. 1 to Sol. 30 were coated onto silicon wafers, followed by heating at 240° C. for 60 seconds, thereby fabricating silicon-containing films Film 1 to Film 30 having thickness of 35 nm, followed by measurement of contact angles (CA1) with pure water, respectively (Table 5).

<Contact Angle Sample of Lower Layer Film at Exposed Portion, after Once Coating a Resist for Negative Development onto the Lower Layer Film, Followed by Exposure, and by Stripping the Resist from the Lower Layer Film>

Silicon-containing resist lower layer film-forming compositions Sol. 1 to Sol. 30 were coated onto silicon wafers, followed by heating at 240° C. for 60 seconds, thereby fabricating silicon-containing films Film 1 to Film 30 having thickness of 35 nm, respectively. These films were subjected to coating thereon of an ArF resist solution (PR-1) for negative development listed in Table 7, followed by baking at 100° C. for 60 seconds, thereby forming photoresist layers each having a thickness of 100 nm, respectively. The photoresist films were subjected to coating thereon of a top coat composition (TC-1) against liquid immersion listed in Table 8, followed by baking at 90° C. for 60 seconds, thereby forming top coats each having a thickness of 50 nm, respectively. Next, the photoresist films were subjected to exposure over whole surfaces thereof by an ArF liquid immersion exposure apparatus (NSR-S610C: manufactured by Nikon Corp.), followed by baking (FEB) at 100° C. for 60 seconds, by discharging of butyl acetate as a developer for 3 seconds from a developing nozzle while rotating the wafers at 30 rpm, by puddle development thereafter for 27 seconds after stopping the rotation, by rinsing by diisoamyl ether, by spindrying thereafter, and by baking at 100° C. for 20 seconds to evaporate the rinsing solvent. Residual resist films were fully rinsed and removed by PGME, followed by obtainment of those portions of silicon-containing films at exposed portions, respectively. These were each subjected to measurement of contact angle with pure water, thereby confirming that the measured values were all the same as the CA1.

<Contact Angle Sample of Exposed Portion of Resist for Negative Development>

ArF resist solutions for negative development (PR-1, PR2) listed in Table 7 were coated onto silicon wafers, and baked at 100° C. for 60 seconds, to fabricate photoresist films each having a thickness of 100 nm, respectively, followed by measurement of contact angle with pure water. Next, the same resist films were subjected to exposure over whole surfaces thereof by an ArF exposure apparatus (NSR-S610C: manufactured by Nikon Corp.), followed by baking (FEB) at 100° C. for 60 seconds, by rinsing by diisoamyl ether, by spindrying thereafter, by baking at 100° C. for 20 seconds to evaporate the rinsing solvent to each fabricate an ArF resist film corresponding to a pattern portion upon negative development from which an acid leaving group(s) had been removed, and finally by measurement of contact angle with pure water (Table 6).

TABLE 5

| No. | Contact angle |
|---|---|
| Film 1 | 54° |
| Film 2 | 50° |
| Film 3 | 49° |
| Film 4 | 51° |
| Film 5 | 51° |
| Film 6 | 53° |
| Film 7 | 53° |
| Film 8 | 54° |
| Film 9 | 52° |
| Film 10 | 50° |
| Film 11 | 51° |
| Film 12 | 53° |
| Film 13 | 53° |
| Film 14 | 52° |
| Film 15 | 52° |
| Film 16 | 51° |
| Film 17 | 53° |
| Film 18 | 51° |
| Film 19 | 50° |
| Film 20 | 53° |
| Film 21 | 53° |
| Film 22 | 50° |
| Film 23 | 53° |
| Film 24 | 53° |
| Film 25 | 53° |
| Film 26 | 53° |
| Film 27 | 54° |
| Film 28 | 51° |
| Film 29 | 63° |
| Film 30 | 70° |

TABLE 6

| No. | Contact angle | No. | Contact angle |
|---|---|---|---|
| Nonexposed PR-1 | 71° | Exposed PR-1 | 53° (CAPR-1) |
| Nonexposed PR-2 | 73° | Exposed PR-2 | 56° (CAPR-2) |

Patterning Test by Negative Development

Formed on silicon wafers were spin-on carbon films ODL-50 (carbon content of 80 mass %) produced by Shin-Etsu Chemical Co., Ltd., respectively, each with a film thickness of 200 nm. Coated thereon were silicon-containing resist lower layer film-forming compositions Sol. 11 to Sol. 30, followed by heating at 240° C. for 60 seconds, thereby fabricating silicon-containing resist lower layer films Film 11 to Film 30, respectively, each with a film thickness of 35 nm.

Next, these silicon-containing films were subjected to coating thereon of an ArF resist solution (PR-1) for negative development listed in Table 7, followed by baking at 100° C. for 60 seconds, thereby forming photoresist layers each having a thickness of 100 nm, respectively. The photoresist films were subjected to coating thereon of a top coat composition (TC-1) against liquid immersion listed in Table 8, followed by baking at 90° C. for 60 seconds, thereby forming top coats each having a thickness of 50 nm, respectively.

Separately, the silicon-containing films were subjected to coating thereon of ArF resist solutions (PR-2, PR-3) for negative development listed in Table 7, followed by baking at 110° C. for 60 seconds, thereby forming photoresist layers each having a thickness of 100 nm, respectively.

Next, the photoresist films were subjected to exposure by an ArF liquid immersion exposure apparatus (NSR-S6100: manufactured by Nikon Corp.; NA of 1.30, σ of 0.98/0.65, 35° dipole polarized illumination, and 6% halftone phase-shift mask), followed by baking (PEB) at 100° C. for 60 seconds, by discharging of butyl acetate as a developer for 3 seconds from a developing nozzle while rotating the wafers at 30 rpm, by puddle development thereafter for 27 seconds after stopping the rotation, by rinsing by diisoamyl ether, by spindrying thereafter, and by baking at 100° C. for 20 seconds to evaporate the rinsing solvent.

Obtained by this patterning were negative line-and-space patterns of 43 nm at 1:1. With this dimension, pattern collapse was measured by an electron microscope (CG4000) manufactured by Hitachi High-Technologies Corporation, and the cross-section shape was measured by an electron microscope (S-4700) manufactured Hitachi, Ltd. (Table 9).

TABLE 7

| No. | Polymer (parts by mass) | Acid generator (parts by mass) | Base (parts by mass) | Water repellent polymer (parts by mass) | Solvent (parts by mass) |
|---|---|---|---|---|---|
| PR-1 | ArF resist polymer 1 (100) | PAG (7.0) | Quencher (1.0) | None | PGMEA (2,500) |
| PR-2 | ArF resist polymer 2 (100) | PAG (7.0) | Quencher (1.0) | None | PGMEA (2,500) |
| PR-3 | ArF resist polymer 2 (100) | PAG (10.0) | Quencher (2.0) | Water repellent polymer 1 (4.0) | PGMEA (2,500) |

ArF resist polymer 1:
Molecular weight (Mw) = 8,600
Dispersity (Mw/Mn) = 1.88

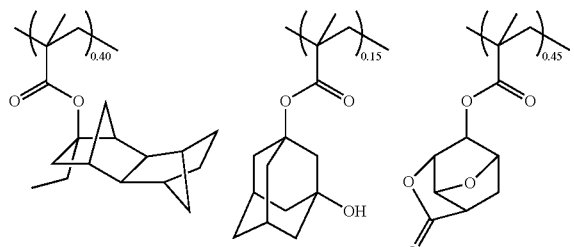

ArF resist polymer 2:
Molecular weight (Mw) = 8,900
Dispersity (Mw/Mn) = 1.93

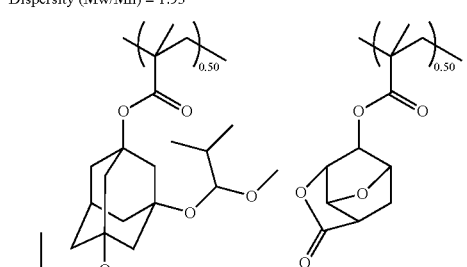

Acid generator: PAG

TABLE 7-continued

| No. | Polymer (parts by mass) | Acid generator (parts by mass) | Base (parts by mass) | Water repellent polymer (parts by mass) | Solvent (parts by mass) |
|---|---|---|---|---|---|

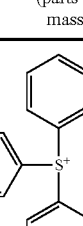

Base: Quencher

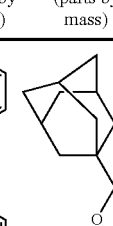

Water repellent polymer 1:
Molecular weight (Mw) = 8,200
Dispersity (Mw/Mn) = 1.67

TABLE 8

| | Polymer (parts by mass) | Organic solvent (parts by mass) |
|---|---|---|
| TC-1 | Protective film polymer (100) | Diisoamyl ether (2700) 2-methyl-1-butanol (270) |

Top coat polymer:
Molecular weight (Mw) = 8,800
Dispersity (Mw/Mn) = 1.69

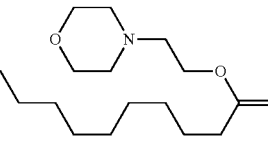

TABLE 9

| | Silicon-containing film | ArF resist | Pattern cross-section shape after development | Pattern collapse | CAPR1-CA1 |
|---|---|---|---|---|---|
| Example 1-1 | Film11 | PR-1 | Vertical | None | −2° |
| Example 1-2 | Film12 | PR-1 | Vertical | None | 0° |
| Example 1-3 | Film13 | PR-1 | Vertical | None | 0° |
| Example 1-4 | Film14 | PR-1 | Vertical | None | −1° |
| Example 1-5 | Film15 | PR-1 | Vertical | None | −1° |
| Example 1-6 | Film16 | PR-1 | Vertical | None | −2° |
| Example 1-7 | Film17 | PR-1 | Vertical | None | 0° |
| Example 1-8 | Film18 | PR-1 | Vertical | None | −2° |
| Example 1-9 | Film19 | PR-1 | Vertical | None | −3° |
| Example 1-10 | Film20 | PR-1 | Vertical | None | 0° |
| Example 1-11 | Film21 | PR-1 | Vertical | None | 0° |
| Example 1-12 | Film22 | PR-1 | Vertical | None | −3° |
| Example 1-13 | Film23 | PR-1 | Vertical | None | 0° |
| Example 1-14 | Film24 | PR-1 | Vertical | None | 0° |
| Example 1-15 | Film25 | PR-1 | Vertical | None | 0° |
| Example 1-16 | Film26 | PR-1 | Vertical | None | 0° |
| Example 1-17 | Film27 | PR-1 | Vertical | None | 1° |
| Example 1-18 | Film28 | PR-1 | Vertical | None | −2° |
| Example 1-19 | Film29 | PR-1 | Vertical | None | 10° |
| Comparative Example 1-1 | Film30 | PR-1 | Vertical | Presence of collapse | 17° |

As listed in Table 9, the silicon-containing films according to the silicon-containing resist lower layer film-forming compositions of the present invention had contact angles (CA1) exhibiting differences of 10 degrees or less relative to the contact angles (CAPR-1) of the upper layer resists after negative development, thereby proving that the latter were free of pattern collapse (Examples 1-1 to 1-19). Particularly, it was exemplified from the results of Example 1-1 and 1-19 that the surface modifier of the present invention was excellent in separation and thus concentratedly present at a surface of the lower layer film upon formation thereof to thereby enable to further approximate the contact angle of the applicable silicon-containing film to the contact angle of the upper layer resist pattern after development, insofar as the ratio of tetrafunctional unit (Monomer 102) in the polysiloxane was 70 mole %.

Contrary, in case of negative development in Comparative Example 1-1 without containing the silicon-containing surface modifier of the present invention, the difference between such contact angles was so large to cause pattern collapse.

Patterning Test: Developer

Instead of the developer (butyl acetate) used in Example 1, the following developers were used to obtain negative line-and-space patterns of 43 nm at 1:1 (Table 10), respectively, in the same procedure as Example 1.

TABLE 10

| | Silicon-Containing film | ArF resist | Developer | Pattern cross-section shape after development | Pattern collapse |
|---|---|---|---|---|---|
| Example 2-1 | Film11 | PR-1 | 2-heptanone | Vertical | None |
| Example 2-2 | Film11 | PR-1 | Methyl benzoate | Vertical | None |
| Example 2-3 | Film11 | PR-2 | Ethyl benzoate | Vertical | None |
| Example 2-4 | Film11 | PR-2 | Phenyl acetate | Vertical | None |
| Example 2-5 | Film11 | PR-3 | Benzyl acetate | Vertical | None |

TABLE 10-continued

| | Silicon-Containing film | ArF resist | Developer | Pattern cross-section shape after development | Pattern collapse |
|---|---|---|---|---|---|
| Example 2-6 | Film11 | PR-3 | Methyl phenylacetate | Vertical | None |

As shown in Table 10, it was possible to obtain resist patterns having cross-section of vertical shape, even by using various developers, respectively.

Pattern Etching Test: Negatively Developed Pattern

Each applicable resist pattern by negative development as fabricated in the above patterning test based on negative development was used as a mask to dry etch the associated silicon-containing film under the following condition (1), and the thus obtained pattern of the silicon-containing film was transferred to the applicable spin-on carbon film by dry etching under the following condition (2). The eventual patterns were observed by an electron microscope (S-9380) manufactured by Hitachi, Ltd. for cross-section shape comparison, and by an electron microscope (CG4000) manufactured by Hitachi High-Technologies Corporation for pattern roughness comparison, the results of which are summarized in Table 11.

(1) Etching Condition by Gas Based on $CHF_3/CF_4$

Apparatus: dry etching apparatus Telius SP manufactured by Tokyo Electron Limited Etching Condition (1):

| | |
|---|---|
| Chamber pressure: | 15 Pa |
| Upper/Lower RF Power: | 500 W/300 W |
| $CHF_3$ gas flow rate: | 50 ml/min |
| $CH_4$ gas flow rate: | 150 ml/min |
| Ar gas flow rate: | 100 ml/min |
| Processing time: | 40 sec |

(2) Etching Condition by Gas Based on $O_2/N_2$

Apparatus: dry etching apparatus Telius SP manufactured by Tokyo Electron Limited Etching Condition (2):

| | |
|---|---|
| Chamber pressure: | 5 Pa |
| Upper/Lower RF Power: | 1,000 W/300 W |
| $O_2$ gas flow rate: | 300 ml/min |
| $N_2$ gas flow rate: | 100 ml/min |
| Ar gas flow rate: | 100 ml/min |
| Processing time: | 30 sec |

TABLE 11

| | Silicon-containing film | ArF resist | Pattern cross-section shape of spin-on carbon film after dry etching | Pattern roughness |
|---|---|---|---|---|
| Example 3-1 | Film11 | PR-1 | Vertical | 1.7 nm |
| Example 3-2 | Film12 | PR-1 | Vertical | 1.6 nm |
| Example 3-3 | Film13 | PR-1 | Vertical | 2.1 nm |
| Example 3-4 | Film14 | PR-1 | Vertical | 1.6 nm |
| Example 3-5 | Film15 | PR-1 | Vertical | 2.2 nm |
| Example 3-6 | Film16 | PR-1 | Vertical | 1.9 nm |
| Example 3-7 | Film17 | PR-1 | Vertical | 1.8 nm |
| Example 3-8 | Film18 | PR-1 | Vertical | 1.9 nm |
| Example 3-9 | Film19 | PR-1 | Vertical | 1.9 nm |
| Example 3-10 | Film20 | PR-1 | Vertical | 1.6 nm |
| Example 3-11 | Film21 | PR-2 | Vertical | 1.8 nm |
| Example 3-12 | Film22 | PR-2 | Vertical | 1.5 nm |
| Example 3-13 | Film23 | PR-2 | Vertical | 2.1 nm |
| Example 3-14 | Film24 | PR-2 | Vertical | 1.9 nm |
| Example 3-15 | Film25 | PR-2 | Vertical | 1.6 nm |
| Example 3-16 | Film26 | PR-2 | Vertical | 2.1 nm |
| Example 3-17 | Film27 | PR-2 | Vertical | 1.9 nm |
| Example 3-18 | Film28 | PR-2 | Vertical | 1.6 nm |
| Example 3-19 | Film29 | PR-2 | Vertical | 2.8 nm |

As listed in Table 11, it was recognized that resist shapes after development, and cross-section shapes and pattern roughness of spin-on carbon films after processing were excellent according to the present invention. Particularly, it was exemplified from the results of Example 3-1 and 3-19 that pattern roughness was further lowered, insofar as the ratio of tetrafunctional unit (Monomer 102) in the polysiloxane was 70 mole %.

It is noted that the present invention is not limited to the above embodiments. The embodiments are illustrative, and whatever have substantially the same configuration as the technical concept recited in the claims of the present application and exhibit the same functions and effects, are embraced within the technical scope of the present invention.

EXPLANATION OF LETTERS OR NUMERALS

1 . . . substance to be processed

1a . . . negative pattern

2 . . . lower organic layer film,

2a . . . negative pattern of lower organic layer film

3 . . . silicon-containing resist lower layer film

3a . . . negative pattern of silicon-containing resist lower layer film

4 . . . photoresist film

4a . . . negative resist pattern

What is claimed is:

1. A silicon-containing resist lower layer film-forming composition comprising:

a polysiloxane compound containing a component derived from a tetrafunctional hydrolyzable monomer in an amount of 70 mole % or more of the polysiloxane compound; and a silicon-containing surface modifier containing one or more repeating units each represented by the following general formula (A), or one or more partial structures each represented by the following general formula (C):

-continued

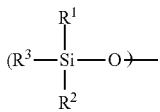
(C)

wherein:
R¹ represents an organic group having a hydroxyl group or a carboxylic acid group; and
R² and R³ each independently represents the same as R¹, a hydrogen atom, or a monovalent organic group having 1 to 30 carbon atoms, wherein a blending amount of the silicon-containing surface modifier in the silicon-containing resist lower layer film-forming composition is 0.01-50 parts by mass with respect to 100 parts by mass of the polysiloxane compound.

2. The silicon-containing resist lower layer film-forming composition according to claim 1, wherein the silicon-containing surface modifier further contains repeating units each represented by the following general formula (B):

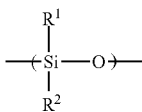
(B)

wherein R¹ and R² represent the same as the above.

3. The silicon-containing resist lower layer film-forming composition according to claim 2, further comprising a solvent having a boiling point of 180° C. or higher.

4. The silicon-containing resist lower layer film-forming composition according to claim 1, further comprising a solvent having a boiling point of 180° C. or higher.

5. A patterning process, comprising:
using a coating type of organic lower layer film material to form a lower organic layer film on a substance to be processed;
using the silicon-containing resist lower layer film-forming composition according to claim 4 to form a silicon-containing resist lower layer film on the lower organic layer film;
using a chemically amplified resist composition to form a photoresist film on the silicon-containing resist lower layer film;
heat-treating the photoresist film, then exposing the photoresist film to a high energy beam, and subsequently using an organic solvent-based developer to dissolve a non-exposed portion of the photoresist film, thereby forming a negative pattern through the photoresist film;
transferring the negative pattern formed through the photoresist film onto the silicon-containing resist lower layer film by dry etching using the photoresist film as a mask;
transferring the thus obtained resist lower layer film pattern onto the lower organic layer film by dry etching using the resist lower layer film as a mask; and
transferring the thus obtained lower organic layer film pattern onto the substance to be processed, by dry etching using the lower organic layer film as a mask.

6. A patterning process, comprising:
forming an organic hard mask containing carbon as a main component, on a substance to be processed, by a CVD technique;
using the silicon-containing resist lower layer film-forming composition according to claim 4 to form a silicon-containing resist lower layer film on the organic hard mask;
using a chemically amplified resist composition to form a photoresist film on the silicon-containing resist lower layer film;
heat-treating the photoresist film, then exposing the photoresist film to a high energy beam, and subsequently using an organic solvent-based developer to dissolve a non-exposed portion of the photoresist film, thereby forming a negative pattern through the photoresist film;
transferring the negative pattern formed through the photoresist film onto the silicon-containing resist lower layer film by dry etching using the photoresist film as a mask;
transferring the thus obtained resist lower layer film pattern onto the organic hard mask by dry etching using the resist lower layer film as a mask; and
transferring the thus obtained organic hard mask pattern onto the substance to be processed, by dry etching using the organic hard mask as a mask.

7. A patterning process, comprising:
using a coating type of organic lower layer film material to form a lower organic layer film on a substance to be processed;
using the silicon-containing resist lower layer film-forming composition according to claim 1 to form a silicon-containing resist lower layer film on the lower organic layer film;
using a chemically amplified resist composition to form a photoresist film on the silicon-containing resist lower layer film;
heat-treating the photoresist film, then exposing the photoresist film to a high energy beam, and subsequently using an organic solvent-based developer to dissolve a non-exposed portion of the photoresist film, thereby forming a negative pattern through the photoresist film;
transferring the negative pattern formed through the photoresist film onto the silicon-containing resist lower layer film by dry etching using the photoresist film as a mask;
transferring the thus obtained resist lower layer film pattern onto the lower organic layer film by dry etching using the resist lower layer film as a mask; and
transferring the thus obtained lower organic layer film pattern onto the substance to be processed, by dry etching using the lower organic layer film as a mask.

8. The patterning process according to claim 7, wherein the substance to be processed is a semiconductor device substrate itself, or a semiconductor device substrate having formed thereon any one of a metal film, an alloy film, a metal carbide film, a metal oxide film, a metal nitride film, a metal oxide carbide film, and a metal oxide nitride film.

9. The patterning process according to claim 8, wherein the substance to be processed includes a constituent metal which is any one of silicon, gallium, titanium, tungsten, hafnium, zirconium, chromium, germanium, copper, aluminum, and iron, or which is an alloy of one or more of these metals.

10. A patterning process, comprising:
forming an organic hard mask containing carbon as a main component, on a substance to be processed, by a CVD technique;
using the silicon-containing resist lower layer film-forming composition according to claim 1 to form a silicon-containing resist lower layer film on the organic hard mask;

using a chemically amplified resist composition to form a photoresist film on the silicon-containing resist lower layer film;

heat-treating the photoresist film, then exposing the photoresist film to a high energy beam, and subsequently using an organic solvent-based developer to dissolve a non-exposed portion of the photoresist film, thereby forming a negative pattern through the photoresist film;

transferring the negative pattern formed through the photoresist film onto the silicon-containing resist lower layer film by dry etching using the photoresist film as a mask;

transferring the thus obtained resist lower layer film pattern onto the organic hard mask by dry etching using the resist lower layer film as a mask; and transferring the thus obtained organic hard mask pattern onto the substance to be processed, by dry etching using the organic hard mask as a mask.

11. The patterning process according to claim 10, wherein the substance to be processed is a semiconductor device substrate itself, or a semiconductor device substrate having formed thereon any one of a metal film, an alloy film, a metal carbide film, a metal oxide film, a metal nitride film, a metal oxide carbide film, and a metal oxide nitride film.

12. The patterning process according to claim 11, wherein the substance to be processed includes a constituent metal which is any one of silicon, gallium, titanium, tungsten, hafnium, zirconium, chromium, germanium, copper, aluminum, and iron, or which is an alloy of one or more of these metals.

* * * * *